(12) United States Patent
Arzeno et al.

(10) Patent No.: US 8,183,254 B2
(45) Date of Patent: May 22, 2012

(54) INHIBITORS OF JNK

(75) Inventors: Humberto Bartolome Arzeno, Cupertino, CA (US); James Patrick Dunn, Los Altos, CA (US); David Michael Goldstein, San Jose, CA (US); Leyi Gong, San Mateo, CA (US); Xiaochun Han, Sunnyvale, CA (US); Joan Heather Hogg, Sunnyvale, CA (US); Alam Jahangir, San Jose, CA (US); Wylie Solang Palmer, Mountain View, CA (US); Deborah Carol Reuter, Los Altos, CA (US); Tania Silva, Sunnyvale, CA (US); Parcharee Tivitmahaisoon, Redwood City, CA (US); Teresa Alejandra Trejo-Martin, Union City, CA (US); Shao-Yong Wu, Cupertino, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 345 days.

(21) Appl. No.: 12/454,210

(22) Filed: May 14, 2009

(65) Prior Publication Data

US 2009/0318484 A1 Dec. 24, 2009

Related U.S. Application Data

(60) Provisional application No. 61/053,896, filed on May 16, 2008.

(51) Int. Cl.
*C07D 401/14* (2006.01)
*A61K 31/506* (2006.01)

(52) U.S. Cl. ...................... 514/275; 544/324
(58) Field of Classification Search .................. 544/324; 514/275
See application file for complete search history.

(56) References Cited

U.S. PATENT DOCUMENTS

2008/0103142 A1 5/2008 Goldstein et al.

FOREIGN PATENT DOCUMENTS

| WO | 2006038001 A1 | 4/2006 |
| WO | 2008068171 A1 | 6/2008 |

OTHER PUBLICATIONS

Bogoyevitch et al., c-Jun N-terminal kinase (JNK) signaling: Recent advances and challenges, Biochimica et Biophysica Acta (BBA)—Proteins & Proteomics, vol. 1804, Issue 3, Mar. 2010, pp. 463-475.*
Simone, Oncology: Introduction, Cecil Textbook of Medicine, 20th Edition, vol. 1, pp. 1004-1010, 1996.*
Alam, M., et al. "Synthesis and SAR of Aminopyrimidines as Novel c-Jun N-terminal Kinase (JNK) Inhibitors," Bioorganic & Medicinal Chemistry Letters, 2007, vol. 17 (12) pp. 3463-3467.

* cited by examiner

*Primary Examiner* — Deepak Rao
(74) *Attorney, Agent, or Firm* — George W. Johnston; Dennis P. Tramaloni; Jennifer L. Kisko

(57) ABSTRACT

The invention relates to prodrugs of JNK inhibitors and corresponding methods, formulations, and compositions for inhibiting JNK and treating JNK-mediated disorders. The application discloses prodrugs of JNK inhibitors, as described below in formula I:

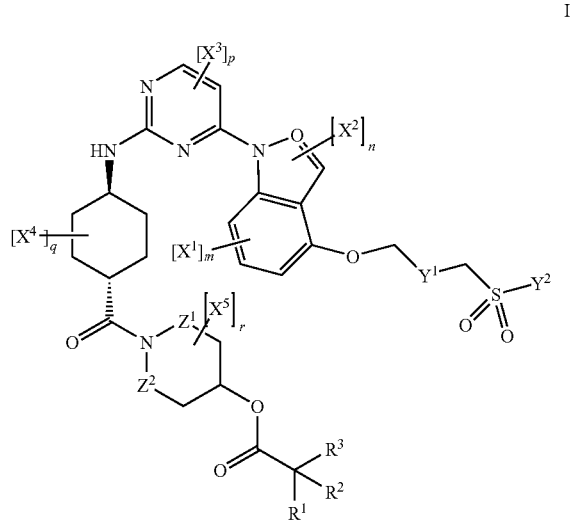

wherein m, n, p, q, Q, r, $R^1$, $R^2$, $R^3$, X, $X^1$, $X^2$, $X^3$, $X^4$, $X^5$, $Y^1$, $Y^2$, $Z^1$ and $Z^2$ are as defined herein. The compounds and compositions disclosed herein are useful to modulate the activity of JNK and treat diseases associated with JNK activity. Disclosed are methods and formulations for inhibiting JNK and treating JNK-mediated disorders, and the like, with the compounds, and processes for making said compounds, and corresponding compositions, disclosed herein.

22 Claims, No Drawings

INHIBITORS OF JNK

CROSS-REFERENCE TO RELATED APPLICATIONS

This application is entitled to the benefit of U.S. provisional patent application Ser. No. 61/053,896 filed on May 16, 2008, the disclosure of which is incorporated herein by reference.

FIELD OF THE INVENTION

This invention relates generally to the fields of medicinal chemistry and treatment of inflammatory disorders. More particularly, the invention relates to prodrugs of JNK inhibitors, processes for making said inhibitors, and corresponding methods, formulations, and compositions for inhibiting JNK and treating JNK-mediated disorders, and the like.

BACKGROUND OF THE INVENTION

JNK The c-Jun N-terminal kinases (JNKs) are members of mitogen-activated protein kinase family along with p38 and extracellular signal-regulated kinases (ERKs). Three distinct genes (jnk1, jnk2 and jnk3) encoding 10 splice variants have been identified. JNK1 and JNK2 are expressed in a wide variety of tissues, whereas JNK3 is mainly expressed in neurons, and to a lesser extent in heart and testes. Members of JNK family are activated by pro-inflammatory cytokines such as tumor necrosis factor α (TNF-α) and interleukin-1β (IL-1β), as well as environmental stresses. The activation of JNKs is mediated by its upstream kinases, MKK4 and MKK7, via dual phosphorylation of Thr-183 and Tyr-185. It has been shown that MKK4 and MKK7 can be activated by the diverse upstream kinases, including MEKK1 and MEKK4, depending upon the external stimuli and cellular context. The specificity of JNK signaling is achieved by forming a JNK-specific signaling complex containing multiple components of the kinase cascade by use of scaffold proteins called JNK-interacting proteins. JNKs have been shown to play important roles in inflammation, T cell functions, apoptosis and cellular survival by phosphorylating specific substrates, including transcription factors such as c-Jun, the component of activator protein-1 (AP1) family, and ATF2, as well as non-transcription factors such as IRS-1 and Bcl-2. Over-activation of JNK is believed to be an important mechanism in autoimmune, inflammatory, metabolic, neurological diseases as well as cancer.

Rheumatoid arthritis (RA) is a systemic autoimmune disease characterized by chronic inflammation of the joints. In addition to the joint swelling and pain caused by the inflammatory process, most RA patients ultimately develop debilitating joint damage and deformation. Several lines of compelling pharmacological and genetic evidence in cellular and animal models strongly suggest the relevance and importance of the activated JNK in the pathogenesis of RA. First, abnormal activation of JNK was detected in both human arthritic joints from RA patients and rodent arthritic joints from animal models of arthritis. In addition, inhibition of JNK activation by selective JNK inhibitors blocked proinflammatory cytokines and MMP production in human synoviocytes, macrophages and lymphocytes. Importantly, administration of the selective JNK inhibitors in rats with adjuvant arthritis or in mice with collagen-induced arthritis effectively protected joints from destruction and significantly reduced paw swelling by inhibiting cytokine and collagenase expression.

Asthma is a chronic inflammatory disease of airways, characterized by the presence of a cellular inflammatory process and by bronchial hyper-responsiveness associated with structural changes of the airways. This disorder has been shown to be driven by many cell types in the airways, including T lymphocytes, eosinophils, mast cells, neutrophils and epithelial cells. JNKs have emerged as promising therapeutic targets for asthma based upon the recent proof-of-concept studies: it has been shown that JNK inhibitors significantly blocked RANTES production in activated human airway smooth cells. More importantly, the JNK inhibitors showed good efficacy in chronic rat and mouse models for their abilities to reduce cellular infiltration, inflammation, hyper-responsiveness, smooth muscle proliferation, and IgE production. These observations suggest important roles of JNKs in the allergic inflammation, airway remodeling process associated with hyper-responsiveness. Therefore, blockade of JNK activity is expected to be beneficial for the treatment of asthma.

Type 2 diabetes is the most serious and prevalent metabolic disease characterized by insulin resistance and insulin secretion impairment as a result of chronic low-level inflammation and abnormal lipid metabolism associated with oxidative stress. It has been reported that JNK activity is abnormally elevated in various diabetic target tissues under obese and diabetic conditions. Activation of the JNK pathway by pro-inflammatory cytokines and oxidative stresses negatively regulates insulin signaling via phosphorylation of insulin receptor substrate-1 (IRS-1) at $Ser^{307}$, therefore contributes to insulin resistance and glucose tolerance. Compelling genetic evidence came from elegant animal model studies using $jnk^{-/-}$ mice crossed with either genetic (ob/ob) obese mice or dietary obese mice. Loss of JNK1($JNK1^{-/-}$), but not JNK2 functions ($jnk2^{-/-}$), protected obese mice from body gains, increased steady-state levels of blood glucose, and decreased plasma insulin levels. These studies demonstrated the potential utility of JNK inhibitor in the treatment of obesity/type 2 diabetes.

Neurodegenerative diseases, such as Alzheimer's (AD), Parkinson's (PD) and Stroke are CNS diseases characterized by synaptic loss, neuronal atrophy and death. The JNK pathway leading to c-Jun activation has been shown to play a causal role in apoptosis of isolated primary embryonic neurons and multiple neuronal cell lines upon induction of a variety of stimuli. Over-activation of JNK was observed in human brains from AD patients or rodent brain sections derived from animal models of neurodegenerative diseases. For example, increased phospho-JNKs were detected in the post-mortem brains from the AD patients. Administration of JNK inhibitory peptide (JIP-1 peptide) in the rodent model of AD induced by β-amyloid peptide administration prevented the impairment of synaptic plasticity. In the animal models of PD (MPTP model), elevated phospho-MKK4 and phospho-JNKs were observed concomitantly with the neuronal cell death. Adenoviral gene transfer of JNK inhibitory peptide (JIP-1 peptide) into striatum of mice attenuated behavioral impairment by inhibiting MPTP-mediated JNK, c-Jun and caspase activation, therefore blocking neuronal cell death in the substantia nigra. In addition, in the animal model of ischemic stroke induced by glutamate excitotoxicity, mice deficient in JNK3, but not JNK1 or JNK2, were resistant to kainic acid (glutamate receptor agonist)-mediated seizure or neuronal death. These data suggest JNK3 was mainly responsible for glutamate excitotoxicity, an important component in ischemic conditions. Taken together, data has emerged suggesting JNKs as attractive target for multiple CNS diseases associated with neuronal cell death.

Uncontrolled cellular growth, proliferation and migration along with de-regulated angiogenesis lead to the formation of malignant tumors. The JNK signal transduction pathway may not act exclusively in apoptosis, sustained JNK activation leading to AP1 activation has recently been implicated to contribute to the cellular survival of specific cancer types such as glial tumors and BCL-ABL transformed B lymphoblasts. In the case of glial tumors, enhanced JNK/AP1 activity was seen in most of the primary brain tumor samples. For the transformed B lymphoblasts, BCL-ABL was shown to activate the JNK pathway which in turn up-regulated expression of anti-apoptotic bcl-2 gene. Interestingly, the multi-drug resistance and hyper-proliferation seen in treatment-refractory AML (acute myeloid leukemia) patients has been causally linked to the sustained JNK activity present in these AML samples. Activation of JNK in leukemic cells resulted in induced expression of efflux pumps such as mdr1 and MRP1 responsible for multidrug resistance. Also, genes with a survival benefit in response to oxidative stress including glutathione-S-transferase π and γ-glutamyl cysteine synthase were also upregulated by the activated JNK pathway.

SUMMARY OF THE INVENTION

In one aspect, the application provides a compound of formula I

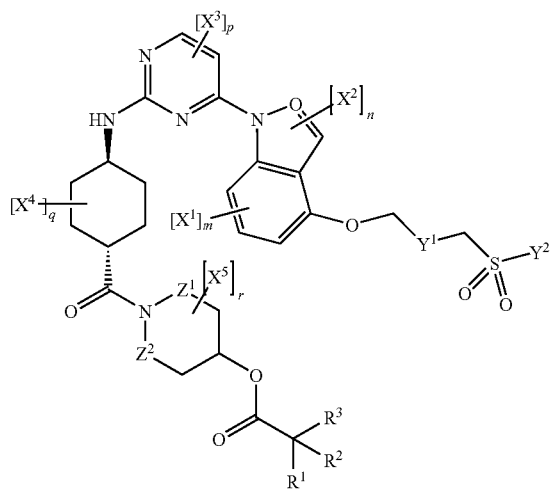

or a pharmaceutically acceptable salt thereof,
wherein:
each of $R^1$ and $R^2$ is independently H or lower alkyl;
or $R^1$ and $R^2$ together form a cycloalkyl ring, optionally substituted with one or more $R^{2'}$;
  $R^{2'}$ is lower alkyl, hydroxy, halogen, amino, lower alkoxy, lower hydroxyalkyl, or lower haloalkyl;
$R^3$ is H or $N(R^4)(R^5)$;
  $R^4$ is H, lower alkyl, or $C(=O)OR^{4'}$;
  $R^{4'}$ is H or lower alkyl;
  $R^5$ is H or lower alkyl;
or $R^2$ and $R^3$ together form a heterocyclic or heteroaryl ring, optionally substituted with one or more $R^{2'}$;
Q is CH or N;
$Z^1$ is $(CH_2)_u$;
  u is 0 or 1;
$Z^2$ is $(CH_2)_v$;
  v is 0 or 1;
$X^1$ is lower alkyl, lower alkoxy, lower haloalkyl, or hydroxy;
m is 0, 1, or 2;
$X^2$ is lower alkyl, lower alkoxy, or lower haloalkyl;
n is 0 or 1;
$X^3$ is lower alkyl, lower alkoxy, or lower haloalkyl;
p is 0 or 1;
$X^4$ is lower alkyl, lower alkoxy, lower haloalkyl, hydroxy, lower hydroxylalkyl, or halogen;
q is 0, 1, or 2;
$X^5$ is lower alkyl, lower alkoxy, lower haloalkyl, hydroxy, lower hydroxylalkyl, or halogen;
r is 0, 1, or 2;
$Y^1$ is $CH(Y^{1'})$;
  $Y^{1'}$ is H or lower alkyl;
$Y^2$ is H or $Y^{2'}$;
  $Y^{2'}$ is lower alkyl, $N(Y^{2''})_2$, lower haloalkyl, or lower heteroalkyl;
  or $Y^{1'}$ and $Y^{2'}$ together form a heterocyclic ring; and
  each $Y^{2''}$ is independently H, lower alkyl, lower cycloalkyl, phenyl, or lower heterocycloalkyl;
  or both $Y^{2''}$ together form a heterocyclic ring.

In certain embodiments of the above compound, m is 0, n is 0, p is 0, Q is CH, q is 0, $R^1$ is H, r is 0, u is 1, v is 1, $Y^{1'}$ is H, $Y^2$ is $Y^{2'}$, and $Y^{2'}$ is methyl.

In certain embodiments of the compound of formula I, $R^3$ is H.

In certain embodiments of the compound of formula I, $R^2$ is lower alkyl.

In certain embodiments of the compound of formula I, $R^2$ is methyl.

In certain embodiments of the compound of formula I, $R^2$ is methyl and $R^4$ is lower alkyl.

In certain embodiments of the compound of formula I, $R^2$ is methyl and $R^4$ is methyl.

In certain embodiments of the compound of formula I, $R^3$ is lower alkyl.

In certain embodiments of the compound of formula I, $R^3$ is methyl.

In certain embodiments of the compound of formula I, $R^3$ is ethyl.

In certain embodiments of the compound of formula I, $R^4$ is lower alkyl.

In certain embodiments of the compound of formula I, $R^4$ is methyl.

In certain embodiments of the compound of formula I, $R^4$ is ethyl.

In certain embodiments of the compound of formula I, $R^3$ is methyl.

In certain embodiments of the compound of formula I, $R^2$ is H.

In certain embodiments of the compound of formula I, $R^4$ is H.

In certain embodiments of the compound of formula I, $R^2$ is lower alkyl.

In certain embodiments of the compound of formula I, $R^2$ is methyl.

In certain embodiments of the compound of formula I, $R^2$ is iso-propyl.

In certain embodiments of the compound of formula I, $R^2$ is sec-butyl.

In certain embodiments of the compound of formula I, $R^2$ is iso-butyl.

In certain embodiments of the compound of formula I, $R^2$ and $R^3$ come together to form a heterocyclic ring.

In certain embodiments of the compound of formula I, $R^2$ and $R^3$ come together to form a pyrrolidinyl ring.

In certain embodiments of the compound of formula I, $R^4$ is H.

In certain embodiments of the compound of formula I, $R^4$ is lower alkyl.

In certain embodiments of the compound of formula I, $R^4$ is methyl.

In certain embodiments of the compound of formula I, m is 0, n is 0, p is 0, Q is CH, q is 0, $R^1$ is H, r is 0, u is 1, v is 1, $Y^2$ is $Y^{2'}$ and $Y^{1'}$ and $Y^{2'}$ together form a heterocyclic ring.

In certain embodiments of the compound of formula I, m is 0, n is 0, p is 0, Q is CH, q is 0, $R^1$ is H, r is 0, u is 1, v is 1, $Y^{1'}$ is H, $Y^2$ is $Y^{2'}$, $Y^{2'}$ is $N(Y^{2''})_2$, and both $Y^{2''}$ are H.

In one aspect, the application provides a compound of formula II

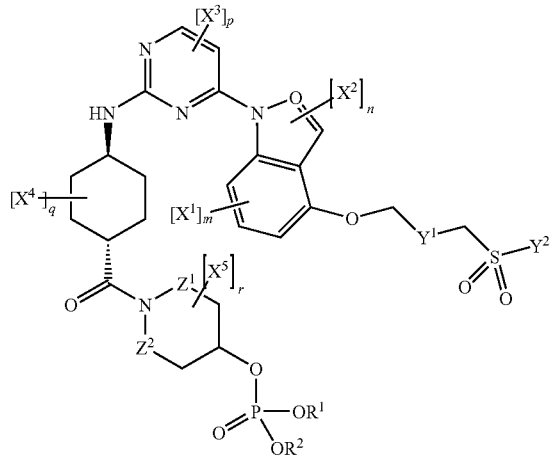

II or a pharmaceutically acceptable salt thereof,
wherein:
$R^1$ and $R^2$ are each independently H or lower alkyl;
Q is CH or N;
$Z^1$ is $(CH_2)_u$;
  u is 0 or 1;
$Z^2$ is $(CH_2)_v$;
  v is 0 or 1;
$X^1$ is lower alkyl, lower alkoxy, lower haloalkyl, or hydroxy;
m is 0, 1, or 2;
$X^2$ is lower alkyl, lower alkoxy, or lower haloalkyl;
n is 0 or 1;
$X^3$ is lower alkyl, lower alkoxy, or lower haloalkyl;
p is 0 or 1;
$X^4$ is lower alkyl, lower alkoxy, lower haloalkyl, hydroxy, lower hydroxylalkyl, or halogen;
q is 0, 1, or 2;
$X^5$ is lower alkyl, lower alkoxy, lower haloalkyl, hydroxy, lower hydroxylalkyl, or halogen;
r is 0, 1, or 2;
$Y^1$ is $CH(Y^{1'})$;
  $Y^{1'}$ is H, lower alkyl, or $Y^{1'}$ and $Y^{2'}$ together form a heterocyclic ring;
$Y^2$ is H or $Y^{2'}$;
  $Y^{2'}$ is lower alkyl, $N(Y^{2''})_2$, lower haloalkyl, or lower heteroalkyl; and
  each $Y^{2''}$ is independently H, lower alkyl, lower cycloalkyl, phenyl, lower heterocycloalkyl, or both $Y^{2''}$ together form a heterocyclic ring.

In certain embodiments of the compound of formula II, m is 0, n is 0, p is 0, Q is CH, q is 0, R is H, r is 0, u is 1, v is 1, $Y^{1'}$ is H, $Y^2$ is $Y^{2'}$, and $Y^{2'}$ is methyl.

In certain embodiments of the compound of formula II, $R^2$ is H.

In certain embodiments of the compound of formula II, $R^2$ is lower alkyl.

In certain embodiments of the compound of formula II, $R^2$ is methyl.

In certain embodiments of the compound of formula II, m is 0, n is 0, p is 0, Q is CH, q is 0, $R^1$ is lower alkyl, r is 0, u is 1, v is 1, $Y^{1'}$ is H, $Y^2$ is methyl, $Z^1$ is $CH_2$, and $Z^2$ is $CH_2$.

In certain embodiments of the compound of formula II, $R^1$ is methyl.

In certain embodiments of the compound of formula II, $R^2$ is lower alkyl.

In certain embodiments of the compound of formula II, $R^1$ is methyl and $R^2$ is lower alkyl.

In certain embodiments of the compound of formula II, $R^1$ is methyl and $R^2$ is methyl.

In one aspect, the application provides a compound of formula III

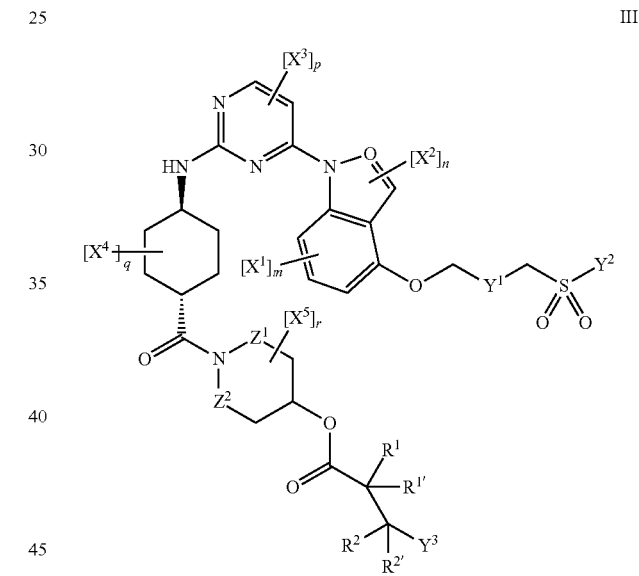

III or a pharmaceutically acceptable salt thereof,
wherein:
$R^1$ and $R^{1'}$ are each independently H or lower alkyl;
$R^2$ is H or lower alkyl;
$R^{2'}$ and $R^3$ are each independently H or lower alkyl, or $R^{2'}$ and $R^3$ together form a heterocyclic ring, optionally substituted with one or more $R^{3'}$;
$R^{3'}$ is lower alkyl, hydroxy, halogen, lower heteroalkyl, lower alkoxy, lower hydroxyalkyl, or lower haloalkyl;
$R^4$ and $R^5$ are each independently H or lower alkyl;
Q is CH or N;
$Z^1$ is $(CH_2)_u$;
  u is 0 or 1;
$Z^2$ is $(CH_2)_v$;
  v is 0 or 1;
$X^1$ is lower alkyl, lower alkoxy, lower haloalkyl, or hydroxy;
m is 0, 1, or 2;
$X^2$ is lower alkyl, lower alkoxy, or lower haloalkyl;
n is 0 or 1;
$X^3$ is lower alkyl, lower alkoxy, or lower haloalkyl;

p is 0 or 1;
$X^4$ is lower alkyl, lower alkoxy, lower haloalkyl, hydroxy, lower hydroxylalkyl, or halogen;
q is 0, 1, or 2;
$X^5$ is lower alkyl, lower alkoxy, lower haloalkyl, hydroxy, lower hydroxylalkyl, or halogen;
r is 0, 1, or 2;
$Y^1$ is $CH(Y^{1'})$;
$Y^{1'}$ is H or lower alkyl;
$Y^2$ is H or $Y^{2'}$;
$Y^{2'}$ is lower alkyl, $N(Y^{2''})_2$, lower haloalkyl, or lower heteroalkyl;
or $Y^{1'}$ and $Y^{2'}$ together form a heterocyclic ring;
each $Y^{2''}$ is independently H, lower alkyl, lower cycloalkyl, phenyl, or lower heterocycloalkyl;
or both $Y^{2''}$ together form a heterocyclic ring; and
$Y^3$ is $N(R^3)(R^4)$ or $N(R^3)(R^4)(R^5)^+$.

In certain embodiments of the compound of formula III, m is 0, n is 0, p is 0, Q is CH, q is 0, $R^1$ is H, r is 0, u is 1, v is 1, $Y^{1'}$ is H, $Y^2$ is $Y^{2'}$, and $Y^{2'}$ is methyl.

In one aspect, the application provides a compound of formula IV

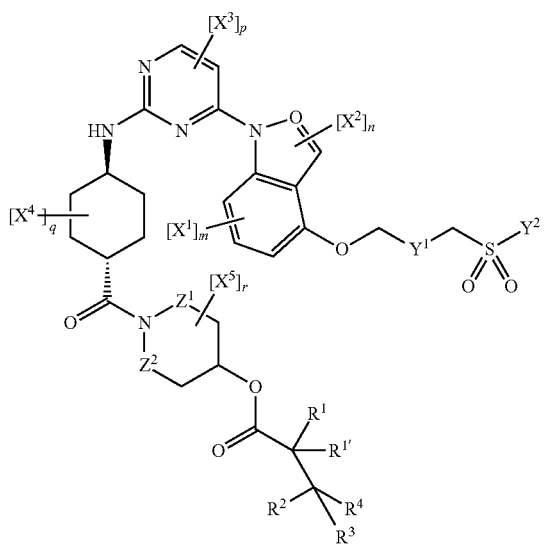

IV or a pharmaceutically acceptable salt thereof,
wherein:
$R^1$ and $R^{1'}$ are each independently H or lower alkyl;
$R^2$ and $R^3$ are each independently H or lower alkyl;
$R^4$ is H, lower alkyl, lower alkoxy, or —C(=O)$OR^1$;
Q is CH or N;
$Z^1$ is $(CH_2)_u$;
 u is 0 or 1;
$Z^2$ is $(CH_2)_v$;
 v is 0 or 1;
$X^1$ is lower alkyl, lower alkoxy, lower haloalkyl, or hydroxy;
m is 0, 1, or 2;
$X^2$ is lower alkyl, lower alkoxy, or lower haloalkyl;
n is 0 or 1;
$X^3$ is lower alkyl, lower alkoxy, or lower haloalkyl;
p is 0 or 1;
$X^4$ is lower alkyl, lower alkoxy, lower haloalkyl, hydroxy, lower hydroxylalkyl, or halogen;
q is 0, 1, or 2;
$X^5$ is lower alkyl, lower alkoxy, lower haloalkyl, hydroxy, lower hydroxylalkyl, or halogen;
r is 0, 1, or 2;
$Y^1$ is $CH(Y^{1'})$;
 $Y^{1'}$ is H or lower alkyl;
$Y^2$ is H or $Y^{2'}$;
 $Y^{2'}$ is lower alkyl, $N(Y^{2''})_2$, lower haloalkyl, or lower heteroalkyl;
or $Y^{1'}$ and $Y^{2'}$ together form a heterocyclic ring; and
 each $Y^{2''}$ is independently H, lower alkyl, lower cycloalkyl, phenyl, or lower heterocycloalkyl;
or both $Y^{2''}$ together form a heterocyclic ring.

In certain embodiments of the compound of formula IV, m is, 0, n is 0, p is 0, Q is CH, q is 0, $R^1$ is H, r is 0, u is 1, v is 1, $Y^{1'}$ is H, $Y^2$ is $Y^{2'}$, and $Y^{2'}$ is methyl.

In one aspect, the application provides a compound of formula V

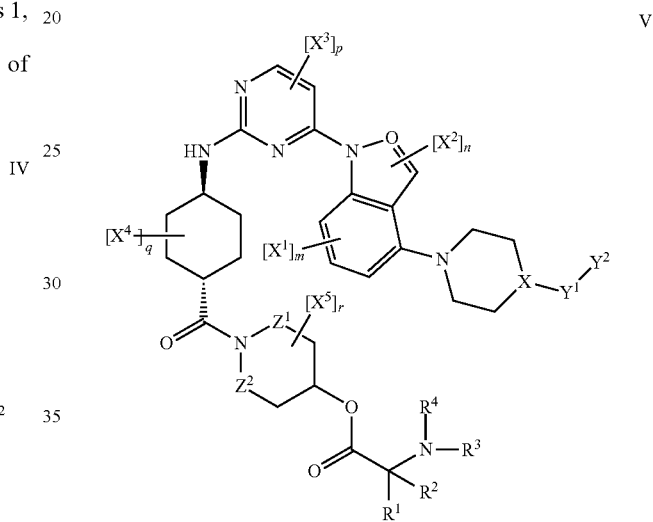

V or a pharmaceutically acceptable salt thereof,
wherein:
$R^1$ is H or lower alkyl, or $R^1$ and $R^2$ together form a cycloalkyl ring, optionally substituted with one or more $R^{2'}$;
 $R^{2'}$ is lower alkyl, hydroxy, halogen, lower heteroalkyl, lower alkoxy, lower hydroxyalkyl, or lower haloalkyl;
$R^2$ and $R^3$ are each independently H or lower alkyl, or $R^2$ and $R^3$ together form a heterocyclic ring, optionally substituted with one or more $R^{2'}$;
$R^4$ is H or lower alkyl;
Q is CH or N;
$Z^1$ is $(CH_2)_u$;
 u is 0 or 1;
$Z^2$ is $(CH_2)_v$;
 v is 0 or 1;
X is N or CH;
$X^1$ is lower alkyl, lower alkoxy, lower haloalkyl, or hydroxy;
m is 0, 1, or 2;
$X^2$ is lower alkyl, lower alkoxy, or lower haloalkyl;
n is 0 or 1;
$X^3$ is lower alkyl, lower alkoxy, or lower haloalkyl;
p is 0 or 1;
$X^4$ is lower alkyl, lower alkoxy, lower haloalkyl, hydroxy, lower hydroxylalkyl, or halogen;
q is 0, 1, or 2;
$X^5$ is lower alkyl, lower alkoxy, lower haloalkyl, hydroxy, lower hydroxylalkyl, or halogen;

r is 0, 1, or 2;
Y$^1$ is C(=O) or S(=O)$_2$;
Y$^2$ is H or Y$^{2'}$;
Y$^{2'}$ is lower alkyl, N(Y$^{2''}$)$_2$, lower haloalkyl, or lower heteroalkyl; and
each Y$^{2''}$ is independently H, lower alkyl, lower cycloalkyl, phenyl, lower heterocycloalkyl, or both Y$^{2''}$ together form a heterocyclic ring;

In certain embodiments of the compound of formula V, m is 0, n is 0, p is 0, Q is CH, q is 0, R$^1$ is H, r is 0, u is 1, and v is 1.

In certain embodiments of the compound of formula V, X is CH, Y$^1$ is S(=O)$_2$, Y$^2$ is Y$^{2'}$, and Y$^{2'}$ is methyl.

In certain embodiments of the compound of formula V, X is N, Y$^1$ is C(=O), Y$^2$ is Y$^{2'}$, and Y$^{2'}$ is methyl.

In one aspect, the application provides a compound of formula I'

I' or a pharmaceutically acceptable salt thereof,
wherein:
R$^1$ is H or lower alkyl, or R$^1$ and R$^2$ together form a cycloalkyl ring, optionally substituted with one or more R$^{2'}$;
R$^{2'}$ is lower alkyl, hydroxy, halogen, lower heteroalkyl, lower alkoxy, lower hydroxyalkyl, or lower haloalkyl;
R$^2$ and R$^3$ are each independently H or lower alkyl, or R$^2$ and R$^3$ together form a heterocyclic ring, optionally substituted with one or more R$^{2'}$;
R$^4$ is H or lower alkyl;
Q is CH or N;
Z$^1$ is (CH$_2$)$_u$;
u is 0 or 1;
Z$^2$ is (CH$_2$)$_v$;
v is 0 or 1;
X$^1$ is lower alkyl, lower alkoxy, lower haloalkyl, or hydroxy;
m is 0, 1, or 2;
X$^2$ is lower alkyl, lower alkoxy, or lower haloalkyl;
n is 0 or 1;
X$^3$ is lower alkyl, lower alkoxy, or lower haloalkyl;
p is 0 or 1;
X$^4$ is lower alkyl, lower alkoxy, lower haloalkyl, hydroxy, lower hydroxylalkyl, or halogen;
q is 0, 1, or 2;
X$^5$ is lower alkyl, lower alkoxy, lower haloalkyl, hydroxy, lower hydroxylalkyl, or halogen;
r is 0, 1, or 2;
Y$^1$ is CH(Y$^{1'}$);
Y$^{1'}$ is H, lower alkyl, or Y$^{1'}$ and Y$^{2'}$ together form a heterocyclic ring;
Y$^2$ is H or Y$^{2'}$;
Y$^{2'}$ is lower alkyl, N(Y$^{2''}$)$_2$, lower haloalkyl, or lower heteroalkyl; and
each Y$^{2''}$ is independently H, lower alkyl, lower cycloalkyl, phenyl, lower heterocycloalkyl, or both Y$^{2''}$ together form a heterocyclic ring.

In one aspect, the application provides a compound selected from the group consisting of:

-continued
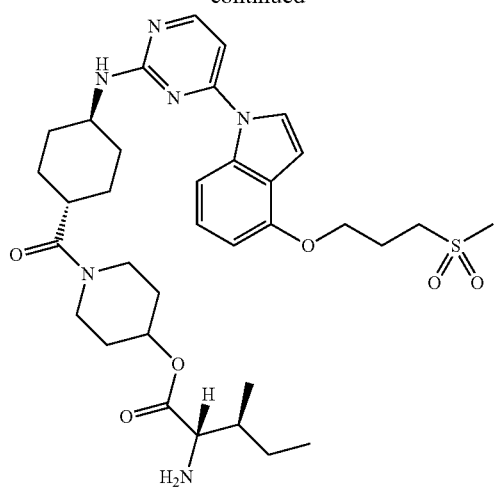
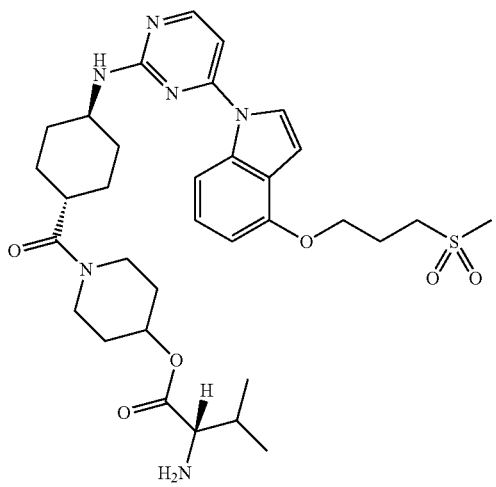
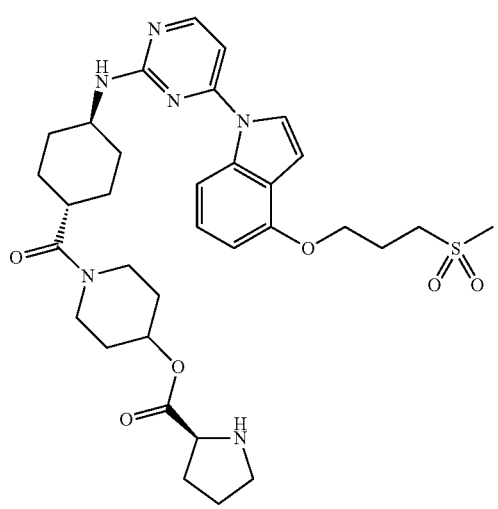
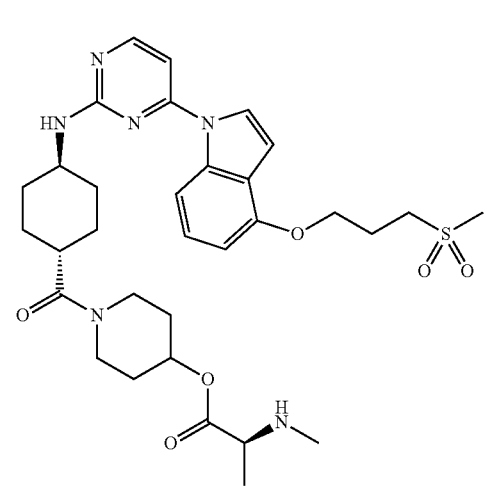
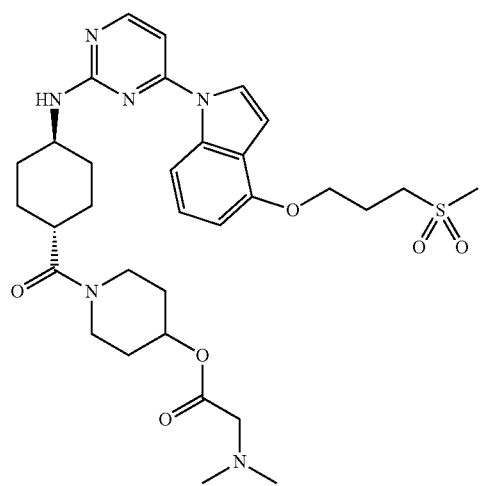
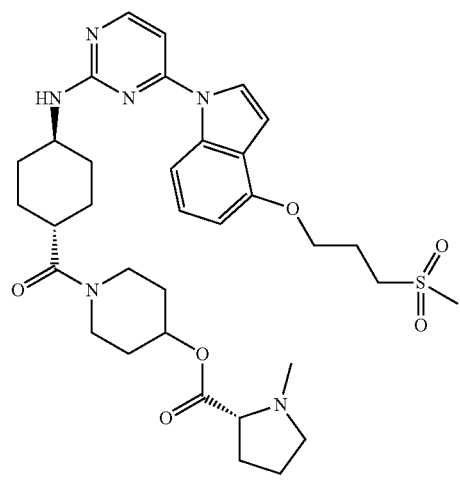

13
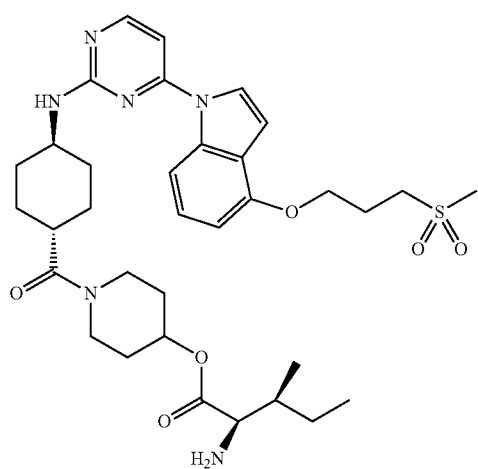
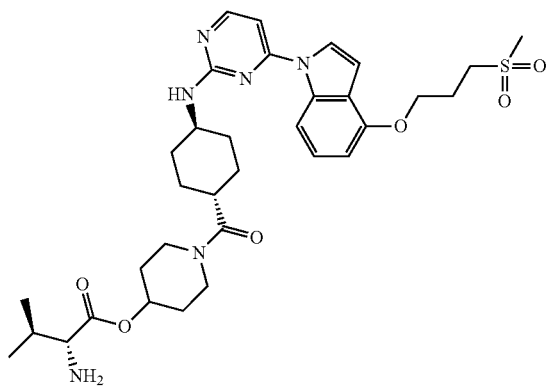
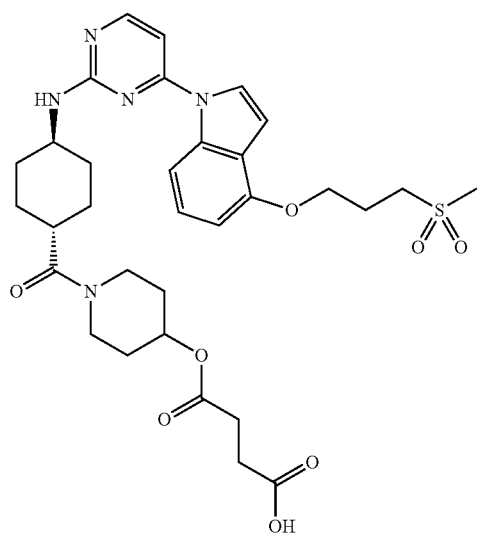
14
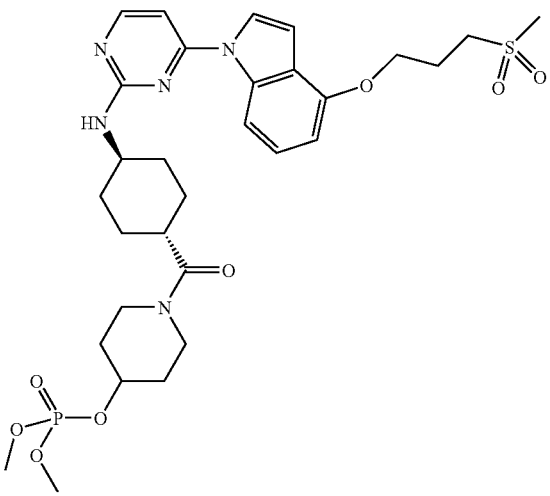
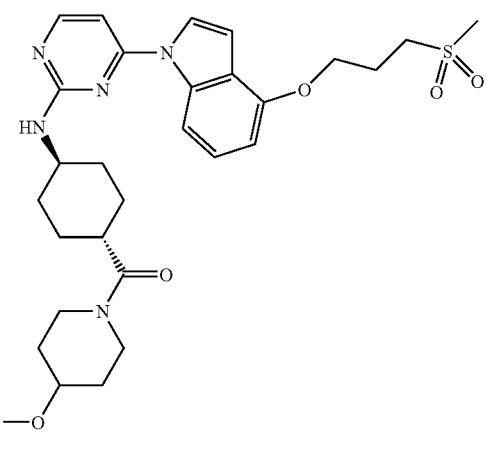

15
-continued
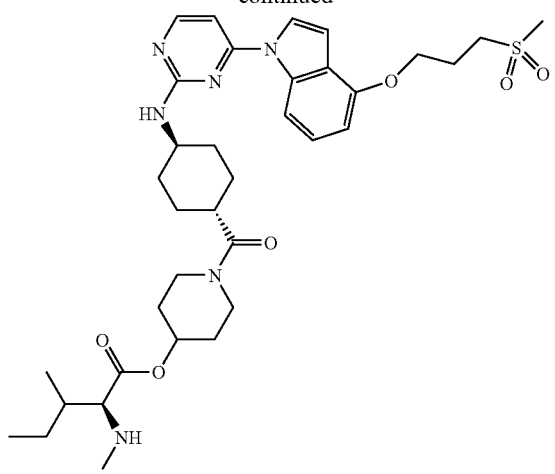
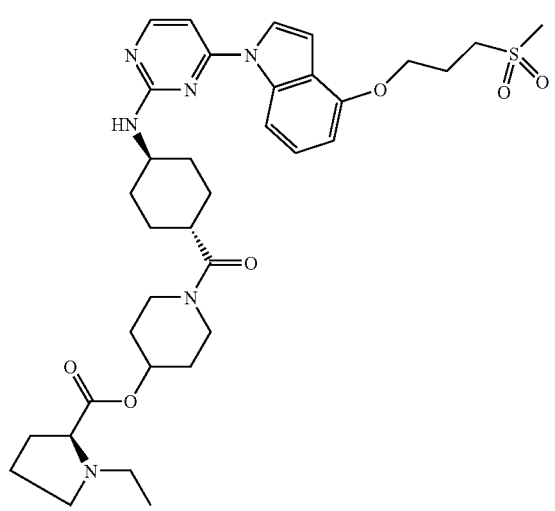
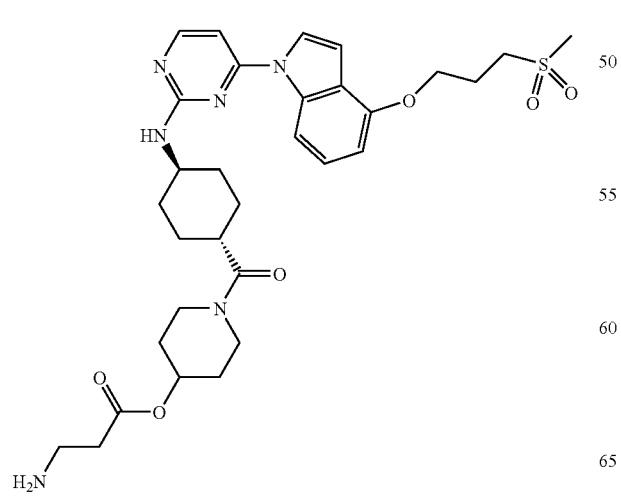
16
-continued
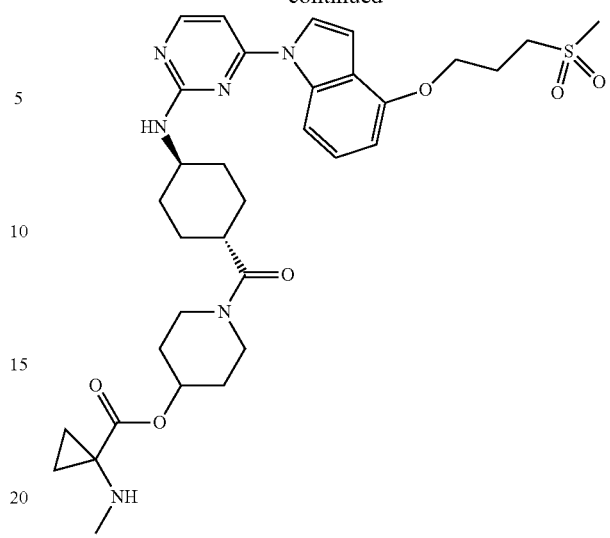
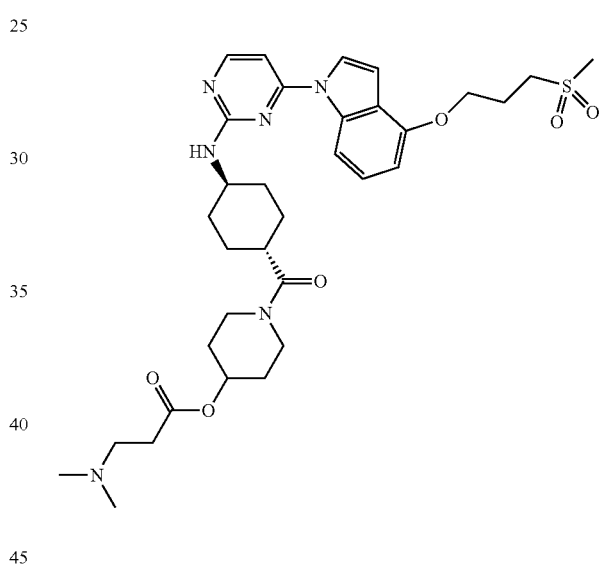
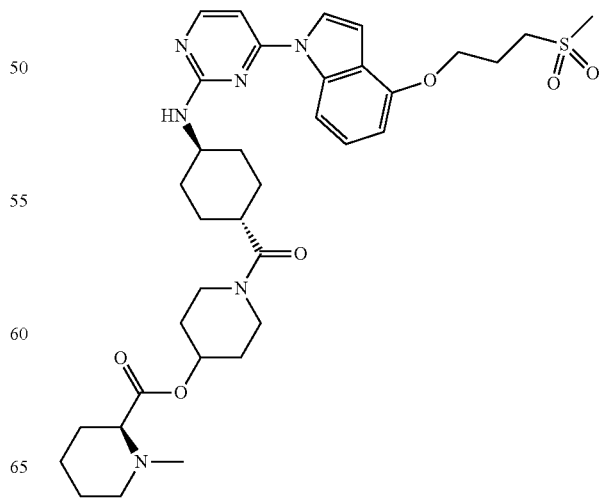

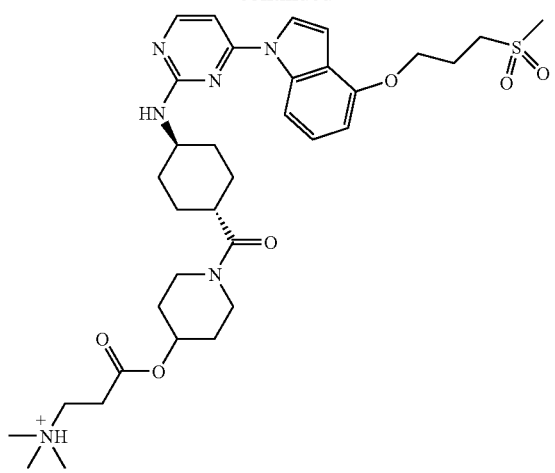
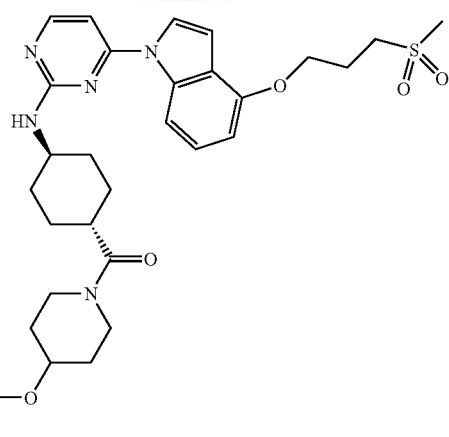

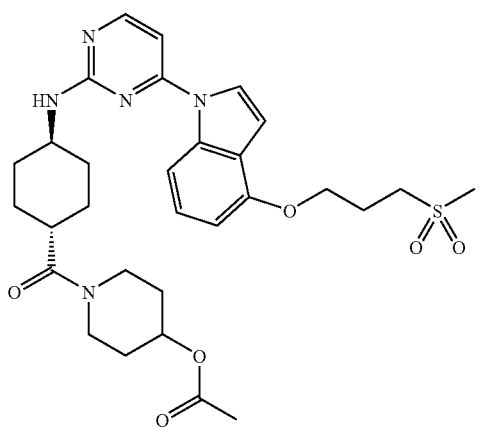

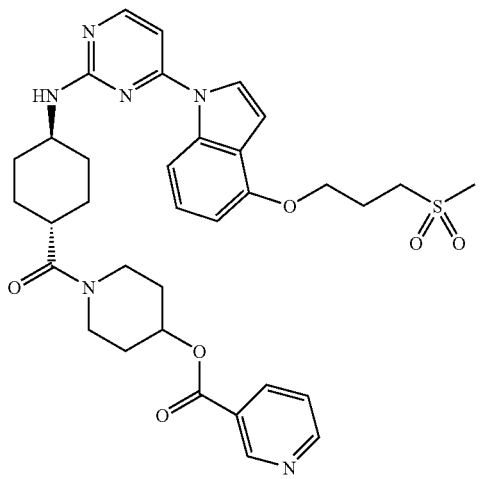

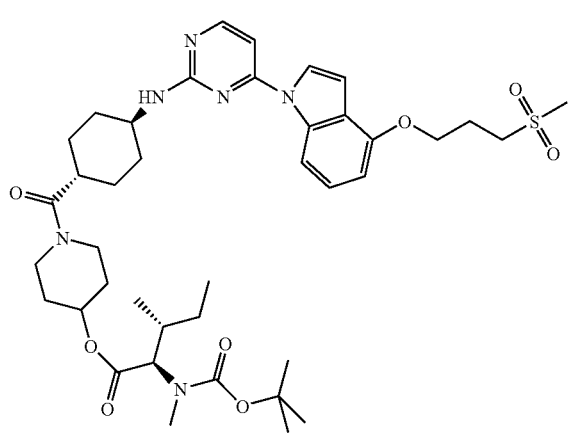

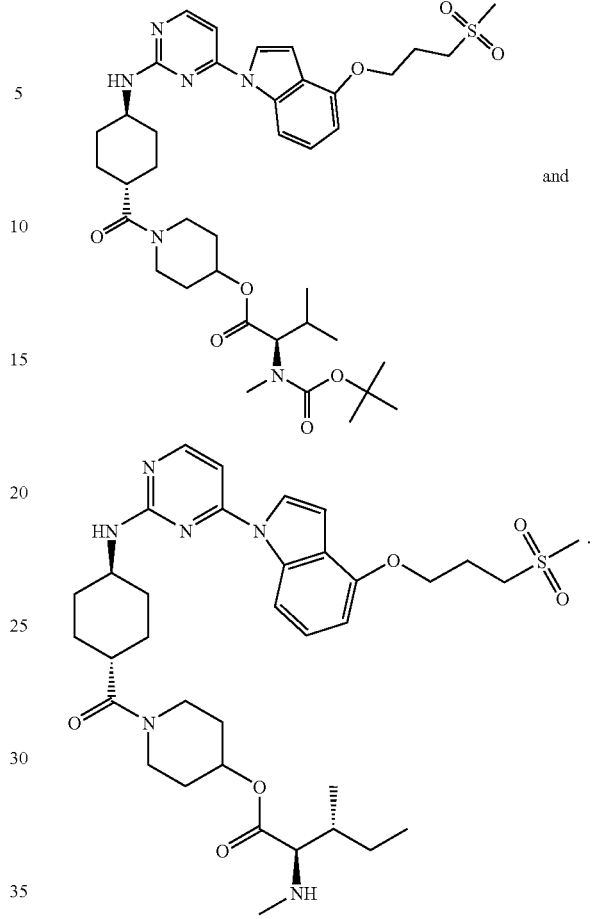

and

The application provides a compound selected from the group consisting of:

(S)-2-Amino-propionic acid 1-(4-{4-[4-(3-methanesulfonyl-propoxy)-indol-1-yl]-pyrimidin-2-ylamino}-cyclohexanecarbonyl)-piperidin-4-yl ester;

2-Amino-2-methyl-propionic acid 1-(4-{4-[4-(3-methanesulfonyl-propoxy)-indol-1-yl]-pyrimidin-2-ylamino}-cyclohexanecarbonyl)-piperidin-4-yl ester;

(S)-2-Amino-4-methyl-pentanoic acid 1-(4-{4-[4-(3-methanesulfonyl-propoxy)-indol-1-yl]-pyrimidin-2-ylamino}-cyclohexanecarbonyl)-piperidin-4-yl ester;

(2S,3S)-2-Amino-3-methyl-pentanoic acid 1-(4-{4-[4-(3-methanesulfonyl-propoxy)-indol-1-yl]-pyrimidin-2-ylamino}-cyclohexanecarbonyl)-piperidin-4-yl ester;

(S)-Pyrrolidine-2-carboxylic acid 1-(4-{4-[4-(3-methanesulfonyl-propoxy)-indol-1-yl]-pyrimidin-2-ylamino}-cyclohexanecarbonyl)-piperidin-4-yl ester;

(S)-2-Amino-3-methyl-butyric acid 1-(4-{4-[4-(3-methanesulfonyl-propoxy)-indol-1-yl]-pyrimidin-2-ylamino}-cyclohexanecarbonyl)-piperidin-4-yl ester;

(R)-1-Methyl-pyrrolidine-2-carboxylic acid 1-(4-{4-[4-(3-methanesulfonyl-propoxy)-indol-1-yl]-pyrimidin-2-ylamino}-cyclohexanecarbonyl)-piperidin-4-yl ester;

Dimethylamino-acetic acid 1-(4-{4-[4-(3-methanesulfonyl-propoxy)-indol-1-yl]-pyrimidin-2-ylamino}-cyclohexanecarbonyl)-piperidin-4-yl ester;

(S)-2-Methylamino-propionic acid 1-(4-{4-[4-(3-methanesulfonyl-propoxy)-indol-1-yl]-pyrimidin-2-ylamino}-cyclohexanecarbonyl)-piperidin-4-yl ester;

(2R,3S)-2-Amino-3-methyl-pentanoic acid 1-(4-{4-[4-(3-methanesulfonyl-propoxy)-indol-1-yl]-pyrimidin-2-ylamino}-cyclohexanecarbonyl)-piperidin-4-yl ester;

(2R,3R)-2-Amino-3-methyl-pentanoic acid 1-(4-{4-[4-(3-methanesulfonyl-propoxy)-indol-1-yl]-pyrimidin-2-ylamino}-cyclohexanecarbonyl)-piperidin-4-yl ester;

Phosphoric acid 1-(4-{4-[4-(3-methanesulfonyl-propoxy)-indol-1-yl]-pyrimidin-2-ylamino}-cyclohexanecarbonyl)-piperidin-4-yl ester dimethyl ester;

Phosphoric acid mono-[1-(4-{4-[4-(3-methanesulfonyl-propoxy)-indol-1-yl]-pyrimidin-2-ylamino}-cyclohexanecarbonyl)-piperidin-4-yl]ester;

Succinic acid mono-[1-(4-{4-[4-(3-methanesulfonyl-propoxy)-indol-1-yl]-pyrimidin-2-ylamino}-cyclohexanecarbonyl)-piperidin-4-yl]ester;

(R)-3-Methyl-2-methylamino-butyric acid 1-(4-{4-[4-(3-methanesulfonyl-propoxy)-indol-1-yl]-pyrimidin-2-ylamino}-cyclohexanecarbonyl)-piperidin-4-yl ester;

(2R,3R)-3-Methyl-2-methylamino-pentanoic acid 1-(4-{4-[4-(3-methanesulfonyl-propoxy)-indol-1-yl]-pyrimidin-2-ylamino}-cyclohexanecarbonyl)-piperidin-4-yl ester;

(S)-1-Ethyl-pyrrolidine-2-carboxylic acid 1-(4-{4-[4-(3-methanesulfonyl-propoxy)-indol-1-yl]-pyrimidin-2-ylamino}-cyclohexanecarbonyl)-piperidin-4-yl ester;

1-Methylamino-cyclopropanecarboxylic acid 1-(4-{4-[4-(3-methanesulfonyl-propoxy)-indol-1-yl]-pyrimidin-2-ylamino}-cyclohexanecarbonyl)-piperidin-4-yl ester;

(S)-1-Methyl-piperidine-2-carboxylic acid 1-(4-{4-[4-(3-methanesulfonyl-propoxy)-indol-1-yl]-pyrimidin-2-ylamino}-cyclohexanecarbonyl)-piperidin-4-yl ester;

3-Amino-propionic acid 1-(4-{4-[4-(3-methanesulfonyl-propoxy)-indol-1-yl]-pyrimidin-2-ylamino}-cyclohexanecarbonyl)-piperidin-4-yl ester;

3-Dimethylamino-propionic acid 1-(4-{4-[4-(3-methanesulfonyl-propoxy)-indol-1-yl]-pyrimidin-2-ylamino}-cyclohexanecarbonyl)-piperidin-4-yl ester;

Trimethylammonium-propionic acid 1-(4-{4-[4-(3-methanesulfonyl-propoxy)-indol-1-yl]-pyrimidin-2-ylamino}-cyclohexanecarbonyl)-piperidin-4-yl ester;

Amino-acetic acid 1-(4-{4-[4-(3-methanesulfonyl-propoxy)-indol-1-yl]-pyrimidin-2-ylamino}-cyclohexanecarbonyl)-piperidin-4-yl ester;

Methylamino-acetic acid 1-(4-{4-[4-(3-methanesulfonyl-propoxy)-indol-1-yl]-pyrimidin-2-ylamino}-cyclohexanecarbonyl)-piperidin-4-yl ester;

Propionic acid 1-(4-{4-[4-(3-methanesulfonyl-propoxy)-indol-1-yl]-pyrimidin-2-ylamino}-cyclohexanecarbonyl)-piperidin-4-yl ester;

(S)-4-Hydroxy-1-methyl-pyrrolidine-2-carboxylic acid 1-(4-{4-[4-(3-methanesulfonyl-propoxy)-indol-1-yl]-pyrimidin-2-ylamino}-cyclohexanecarbonyl)-piperidin-4-yl ester;

(S)-1-Methyl-pyrrolidine-2-carboxylic acid 1-(4-{4-[4-(3-methanesulfonyl-propoxy)-indol-1-yl]-pyrimidin-2-ylamino}-cyclohexanecarbonyl)-piperidin-4-yl ester;

Acetic acid 1-(4-{4-[4-(3-methanesulfonyl-propoxy)-indol-1-yl]-pyrimidin-2-ylamino}-cyclohexanecarbonyl)-piperidin-4-yl ester;

Nicotinic acid 1-(4-{4-[4-(3-methanesulfonyl-propoxy)-indol-1-yl]-pyrimidin-2-ylamino}-cyclohexanecarbonyl)-piperidin-4-yl ester;

(2R,3R)-2-(tert-Butoxycarbonyl-methyl-amino)-3-methyl-pentanoic acid 1(4-{4-[4-(3-methanesulfonyl-propoxy)-indol-1-yl]-pyrimidin-2-ylamino}-cyclohexanecarbonyl)-piperidin-4-yl ester; and (R)-2-(tert-Butoxycarbonyl-methyl-amino)-3-methyl-butyric acid 1-(4-{4-[4-(3-methanesulfonyl-propoxy)-indol-1-yl]-pyrimidin-2-ylamino}-cyclohexanecarbonyl)-piperidin-4-yl ester.

In one aspect, the application provides a method of treating a JNK-mediated disorder in a subject having a JNK-mediated disorder, said method comprising administering to a subject in need thereof a therapeutically effective amount of any of the above compounds.

In certain embodiments of the method of treating a JNK-mediated disorder, the JNK-mediated disorder is characterized by cellular proliferation.

In certain embodiments of the method of treating a JNK-mediated disorder, the JNK-mediated disorder is arthritis.

In certain embodiments of the method of treating a JNK-mediated disorder, the arthritis is rheumatoid arthritis.

In certain embodiments of the method of treating a JNK-mediated disorder, the JNK-mediated disorder is asthma.

In certain embodiments of the method of treating a JNK-mediated disorder, the JNK-mediated disorder is diabetes.

In certain embodiments of the method of treating a JNK-mediated disorder, the JNK-mediated disorder is Alzheimer's disease.

In certain embodiments of the method of treating a JNK-mediated disorder, the JNK-mediated disorder is Parkinson's disease.

In certain embodiments of the method of treating a JNK-mediated disorder, the JNK-mediated disorder is ischemic stroke.

In certain embodiments of the method of treating a JNK-mediated disorder, the JNK-mediated disorder is cancer.

In certain embodiments of the method for treating a JNK-mediated disorder, wherein the JNK-mediated disorder is cancer, the cancer is brain cancer.

In certain embodiments of the method for treating a JNK-mediated disorder, wherein the JNK-mediated disorder is cancer, the cancer is leukemia.

In one aspect, the application provides a pharmaceutical composition comprising the compound of any one of the above embodiments, admixed with at least one pharmaceutically acceptable carrier, excipient or diluent.

In one aspect, the application provides a process for making the compound of formula I, comprising the steps of:

a) reacting 4-(3-methylsulfanyl-propoxy)-1H-indole with 4-chloro-2-methylsulfanyl-pyrimidine;

b) reacting the product of step a) with an oxidizing agent;

c) reacting the product of step b) with 4-amino-cyclohexanecarboxylic acid ethyl ester or pharmaceutically acceptable salt thereof;

d) reacting the product of step c) with a base;

e) reacting the product of step d) with piperidin-4-ol and HBTU; and f) reacting the product of step e) with a substituted or unsubstituted amino acid and HBTU.

In certain embodiments of the above process, the amino acid is proline.

In certain embodiments of the above process, the amino acid is N-methyl proline.

In certain embodiments of the above process, the amino acid is alanine.

In certain embodiments of the above process, the amino acid is N-methyl alanine.

In certain embodiments of the above process, the amino acid is isoleucine.

In certain embodiments of the above process, the amino acid is N-methyl isoleucine.

In certain embodiments of the above process, the amino acid is glycine.

In certain embodiments of the above process, the amino acid is N-methyl glycine.

In certain embodiments of the above process, the amino acid is valine.

In certain embodiments of the above process, the amino acid is N-methyl valine.

In certain embodiments of the above process, the amino acid is leucine.

In certain embodiments of the above process, the amino acid is N-methyl leucine.

In one aspect, the application provides a process for making the compound of formula I, comprising the steps of:

a) reacting 4-(3-methanesulfonyl-propoxy)-1H-indole with 2,4-dichloro-pyrimidine in the presence of HOBt;

b) reacting the product of step a) with 4-amino-cyclohexanecarboxylic acid ethyl ester or pharmaceutically acceptable salt thereof;

c) reacting the product of step b) with a base;

d) reacting the product of step c) with piperidin-4-ol and HBTU; and e) reacting the product of step d) with a substituted or unsubstituted amino acid and HBTU.

In certain embodiments of the above process, the amino acid is proline.

In certain embodiments of the above process, the amino acid is N-methyl proline.

In certain embodiments of the above process, the amino acid is alanine.

In certain embodiments of the above process, the amino acid is N-methyl alanine.

In certain embodiments of the above process, the amino acid is isoleucine.

In certain embodiments of the above process, the amino acid is N-methyl isoleucine.

In certain embodiments of the above process, the amino acid is glycine.

In certain embodiments of the above process, the amino acid is N-methyl glycine.

In certain embodiments of the above process, the amino acid is valine.

In certain embodiments of the above process, the amino acid is N-methyl valine.

In certain embodiments of the above process, the amino acid is leucine.

In certain embodiments of the above process, the amino acid is N-methyl leucine.

DETAILED DESCRIPTION OF THE INVENTION

All publications cited in this disclosure are incorporated herein by reference in their entirety.

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise. Thus, the phrase "'a' or 'an' entity' as used herein refers to one or more of that entity; for example, a compound refers to one or more compounds or at least one compound. As such, the terms "a" (or "an"), "one or more", and "at least one" can be used interchangeably herein.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R's can be nitrogen, or one R" can be carbon and the other nitrogen.

When any variable (e.g., m, n, p, q, Q, r, $R^1$, $R^2$, $R^3$, $R^4$, X, $X^1$, $X^2$, $X^3$, $X^4$, $X^5$, $Y^1$, $Y^2$, $Z^1$, and $Z^2$) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or " ----- " drawn through a bond each refer to the point of attachment of a functional group or other chemical moiety to the rest of the molecule of which it is a part. Thus, for example:

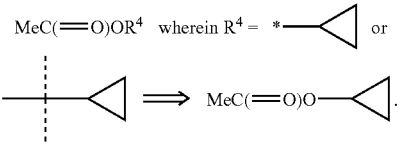

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Certain compounds of the invention may exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇌ —C(—OH)=CH—), amide/imidic acid (—C(=O)—NH— ⇌ —C(—OH)=N—) and amidine (—C(=NR)—NH— ⇌ —C(—NHR)=N—) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics,* 10th Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to either an aryl or a heteroaryl group.

The terms "halo," "halogen," and "halide" are used interchangeably herein and refer to fluoro, chloro, bromo, and iodo.

"Haloalkyl" means alkyl as defined herein in which one or more hydrogen has been replaced with same or different halogen. The term "lower haloalkyl" denotes a straight or branched chain hydrocarbon residue containing 1 to 6 carbon atoms substituted with one or more halogen atom. Exemplary haloalkyls include —CH$_2$Cl, —CH$_2$CF$_3$, —CH$_2$CCl$_3$, —CF$_2$CF$_3$, —CF$_3$, and the like.

The term "acyl" as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term C$_{1-6}$ acyl refers to a group —C(=O)R contain 6 carbon atoms. The term "arylcarbonyl" as used herein means a group of formula C(=O)R wherein R is an aryl group; the term "benzoyl" as used herein an "arylcarbonyl" group wherein R is phenyl.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "C$_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"-, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl" or "aralkyl" are interpreted similarly except R' is an aryl radical. The terms "(het)arylalkyl" or "(het)aralkyl" are interpreted similarly except R' is optionally an aryl or a heteroaryl radical.

The term "alkylene" as used herein denotes a divalent saturated linear hydrocarbon radical of 1 to 10 carbon atoms (e.g., (CH$_2$)$_n$) or a branched saturated divalent hydrocarbon radical of 2 to 10 carbon atoms (e.g., —CHMe- or —CH$_2$CH(i-Pr)CH$_2$—), unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "C$_{1-10}$ alkoxy" as used herein refers to an —O-alkyl wherein alkyl is C$_{1-10}$.

As used herein, "amino acid" refers to a group represented by R'—NH—CH(R)—C(O)—R', R'—NR"—CH(R)—C(O)—R', or [R'—N(R")$_2$—CH(R)—C(O)—R']$^+$, including pharmaceutically acceptable salts thereof, wherein each R" is independently lower alkyl, such as methyl or ethyl, each R' is independently hydrogen, halogen, an aliphatic group, a substituted aliphatic group, an aromatic group, another amino acid, a peptide or a substituted aromatic group. Each R is independently hydrogen or a protected or unprotected side-chain of a naturally-occurring amino acid. Examples of said amino acids include, but are not limited to, alanine, valine, leucine, isoleucine, aspartic acid, glutamic acid, serine, threonine, glutamine, asparagine, arginine, lysine, ornithine, proline, hydroxyproline, phenylalanine, tyrosine, tryptophan, cysteine, methionine and histidine.

An used herein, naturally occurring "amino acid sidechains" include methyl (alanine), isopropyl (valine), sec-butyl (isoleucine), —CH$_2$CH(—CH$_3$)$_2$ (leucine), benzyl (phenylalanine), p-hydroxybenzyl (tyrosine), —CH$_2$—OH (serine), —CHOHCH$_3$ (threonine), —CH$_2$-3-indoyl (tryptophan), —CH$_2$COOH (aspartic acid), —CH$_2$CH$_2$COOH (glutamic acid), —CH$_2$C(O)NH$_2$ (asparagine), —CH$_2$CH$_2$C(O)NH$_2$ (glutamine), —CH$_2$SH, (cysteine), —CH$_2$CH$_2$SCH$_3$ (methionine), —[(CH$_2$)]$_4$NH$_2$ (lysine), —[(CH$_2$)]$_3$NH$_2$ (ornithine), —[(CH)$_2$]$_4$NHC(=NH)NH$_2$ (arginine) and —CH$_2$-3-imidazoyl (histidine).

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

The term "base" includes, but is not limited to, NaOH, KOH, LiOH and alkali metal carbonates such as potassium carbonate, sodium carbonate, lithium carbonate, sodium bicarbonate, cesium carbonate and the like.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof.

"Cycloalkylalkyl" mean a moiety of the formula —$R^a$—$R^b$, where $R^a$ is alkylene and $R^b$ is cycloalkyl as defined herein.

The term "heteroaryl" or "heteroaromatic" as used herein means a monocyclic or bicyclic radical of 5 to 12 ring atoms having at least one aromatic ring containing four to eight atoms per ring, incorporating one or more N, O, or S heteroatoms, the remaining ring atoms being carbon, with the understanding that the attachment point of the heteroaryl radical will be on an aromatic ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidinyl, pyrazinyl, pyrrolyl, pyrazolyl, imidazolyl, oxazol, isoxazole, thiazole, isothiazole, triazoline, thiadiazole and oxadiaxoline which can optionally be substituted with one or more, preferably one or two substituents selected from hydroxy, cyano, alkyl, alkoxy, thio, lower haloalkoxy, alkylthio, halo, haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, quinolinyl, isoquinolinyl, benzofuryl, benzothiophenyl, benzoxazole, benzisoxazole, benzothiazole and benzisothiazole. Bicyclic moieties can be optionally substituted on either ring; however the point of attachment is on a ring containing a heteroatom.

The term "heterocyclyl", "heterocycle", or "heterocycloalkyl" as used herein denotes a monovalent saturated cyclic radical, consisting of one or more rings, preferably one to two rings, of three to eight atoms per ring, incorporating one or more ring heteroatoms (chosen from N,O or $S(O)_{0-2}$), and which can optionally be independently substituted with one or more, preferably one or two substituents selected from hydroxy, oxo, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, unless otherwise indicated. Examples of heterocyclic radicals include, but are not limited to, azetidinyl, pyrrolidinyl, hexahydroazepinyl, oxetanyl, tetrahydrofuranyl, tetrahydrothiophenyl, oxazolidinyl, thiazolidinyl, isoxazolidinyl, morpholinyl, piperazinyl, piperidinyl, tetrahydropyranyl, thiomorpholinyl, quinuclidinyl and imidazolinyl.

The term "hydroxyalkyl" or "lower hydroxy alkyl" as used herein denotes an alkyl radical and lower alkyl radical, respectively, as herein defined, wherein one to three hydrogen atoms on different carbon atoms is/are replaced by hydroxyl groups.

Commonly used abbreviations include: acetyl (Ac), azobis-isobutyrylnitrile (AIBN), atmospheres (Atm), 9-borabicyclo[3.3.1]nonane (9-BBN or BBN), tert-butoxycarbonyl (Boc), di-tert-butyl pyrocarbonate or boc anhydride ($BOC_2O$), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N, N-dimethylaminopyridine (DMAP), N,N-dimethylformamide (DMF), dimethyl sulfoxide (DMSO), 1,1'-bis-(diphenylphosphino) ethane (dppe), 1,1'-bis-(diphenylphosphino)ferrocene (dppf), 1-(3-dimethylaminopropyl)-3-ethylcarbodiimide hydrochloride (EDCI), ethyl (Et), ethyl acetate (EtOAc), ethanol (EtO H), 2-ethoxy-2H-quinoline-1-carboxylic acid ethyl ester (EEDQ), diethyl ether ($Et_2O$), O-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), lithium hexamethyl disilazane (LiHMDS), methanol (MeOH), melting point (mp), $MeSO_2$— (mesyl or Ms), methyl (Me), acetonitrile (MeCN), m-chloroperbenzoic acid (MCPBA), mass spectrum (ms), methyl t-butyl ether (MTBE), N-bromosuccinimide (NBS), N-carboxyanhydride (NCA), N-chlorosuccinimide (NCS), N-methylmorpholine (NMM), N-methylpyrrolidone (NMP), pyridinium chlorochromate (PCC), pyridinium dichromate (PDC), phenyl (Ph), propyl (Pr), iso-propyl (i-Pr), pounds per square inch (psi), pyridine (pyr), room temperature (rt or RT), tert-butyldimethylsilyl or t-$BuMe_2Si$ (TBDMS), triethylamine (TEA or $Et_3N$), 2,2,6,6-tetramethylpiperidine 1-oxyl (TEMPO), triflate or $CF_3SO_2$—(Tf), trifluoroacetic acid (TFA), 1,1'-bis-2,2,6,6-tetramethylheptane-2,6-dione (TMHD), O-benzotriazol-1-yl-N,N,N', N'-tetramethyluronium tetrafluoroborate (TBTU), thin layer chromatography (TLC), tetrahydrofuran (THF), trimethylsilyl or $Me_3Si$ (TMS), p-toluenesulfonic acid monohydrate (TsOH or pTsOH), 4-Me-$C_6H_4SO_2$— or tosyl (Ts), N-urethane-N-carboxyanhydride (UNCA). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

"Preferred "oxidizing agents" include peracids like in-chloroperbenzoic acid (MCPBA) and peracetic acid, but other oxidizing agents like hydrogen peroxide, permanganate salts, or persulfate salts can be used to oxidize a thioether to a sulfone.

"Leaving group" means a group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Agonist" refers to a compound that enhances the activity of another compound or receptor site.

"Antagonist" refers to a compound that diminishes or prevents the action of another compound or receptor site.

The term "drug candidate" refers to a compound or preparation which is to be tested for possible effect in the treatment of a disease state in an animal, regardless of whether said drug candidate has any known biological activity.

The term "homologous" as used herein refers to a protein that performs substantially the same function in another subject species and shares substantial sequence identity, to the extent that they are recognized in the art as being different versions of the same protein, differing primarily in the species in which they are found. Thus, for example, human ERG, mouse ERG, and rat ERG are all considered homologous to each other.

"Modulator" means a molecule that interacts with a target. The interactions include, but are not limited to, agonist, antagonist, and the like, as defined herein.

"Disease" and "Disease state" means any disease, condition, symptom, disorder or indication.

The term "cell line" refers to a clone of immortalized mammalian cells. A "stable" cell line is a cell line that exhibits substantially consistent characteristics over time (e.g., with each doubling). A stable cell line within the scope of this invention provides a substantial proportion of cells that are capable of providing a seal resistance of greater than about 50 MOhm, a current amplitude of greater than about 200 pA, and provide a current amplitude that does not vary by more than approximately 20% over one hour under control conditions.

"Pharmaceutically acceptable salts" of a compound means salts that are pharmaceutically acceptable, as defined herein, and that possess the desired pharmacological activity of the parent compound. Such salts include:

(1) acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or (2) salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

It should be understood that all references to pharmaceutically acceptable salts include solvent addition forms (solvates) or crystal forms (polymorphs) as defined herein, of the same acid addition salt.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" includes mammals and birds. "Mammals" means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgement of the attending medical or veterinary practitioner, and other factors.

"Pharmacological effect" as used herein encompasses effects produced in the subject that achieve the intended purpose of a therapy. For example, a pharmacological effect would be one that results in the prevention, alleviation or reduction of urinary incontinence in a treated subject.

"Disease state" means any disease, condition, symptom, or indication.

"Treating" or "treatment" of a disease state includes (i) preventing the disease state, i.e. causing the clinical symptoms of the disease state not to develop in a subject that may be exposed to or predisposed to the disease state, but does not yet experience or display symptoms of the disease state; (ii) inhibiting the disease state, i.e., arresting the development of the disease state or its clinical symptoms; or (iii) relieving the disease state, i.e., causing temporary or permanent regression of the disease state or its clinical symptoms.

All patents and publications identified herein are incorporated herein by reference in their entirety.

COMPOUNDS AND PREPARATION

Compounds described below are prodrugs of JNK inhibitor (4-hydroxy-piperidin-1-yl)-(4-{4-[4-(3-methanesulfonyl-propoxy)-indol-1-yl]-pyrimidin-2-ylamino}-cyclohexyl)-methanone (I-0), and are useful for inhibiting JNK and treating JNK-mediated disorders, and the like. Examples of representative compounds encompassed by the present invention and within the scope of the invention are provided in Table X as compounds I-1 to I-31 and are prodrugs of the parent drug compound I-0:

I-0

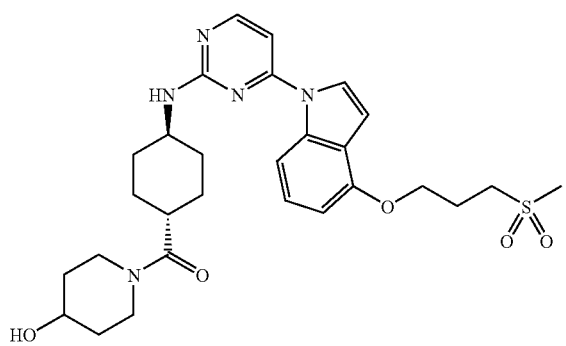

These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE X

| Compound | Nomenclature | Structure | Melting point |
|---|---|---|---|
| I-1 | (S)-2-Amino-propionic acid 1-(4-{4-[4-(3-methanesulfonyl-propoxy)-indol-1-yl-pyrimidin-2-ylamino}-cyclohexanecarbonyl)-piperidin-4-yl ester | 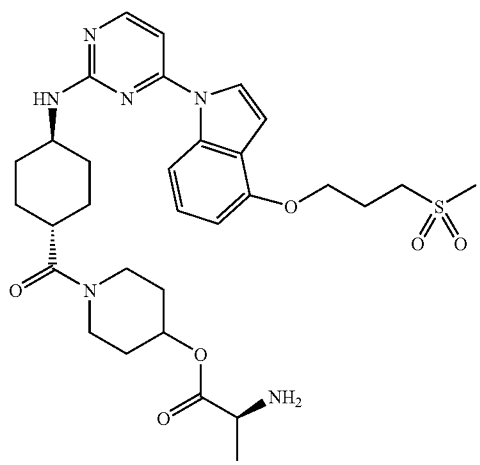 | 202.2-203.2 |
| I-2 | 2-Amino-2-methyl-propionic acid 1-(4-{4-[4-(3-methanesulfonyl-propoxy)-indol-1-yl]-pyrimidin-2-ylamino}-cyclohexanecarbonyl)-piperidin-4-yl ester | 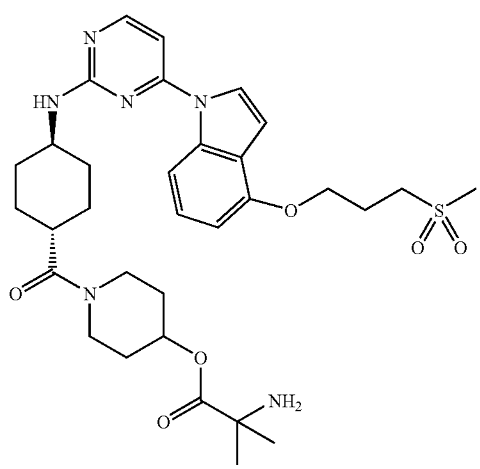 | 219.0-220.0 |

TABLE X-continued

| Compound | Nomenclature | Structure | Melting point |
|---|---|---|---|
| I-3 | (S)-2-Amino-2-methyl-pentanoic acid 1-(4-{4-[4-(3-methanesulfonyl-propoxy)-indol-1-yl]-pyrimidin-2-ylamino}-cyclohexanecarbonyl)-piperidin-4-yl ester | 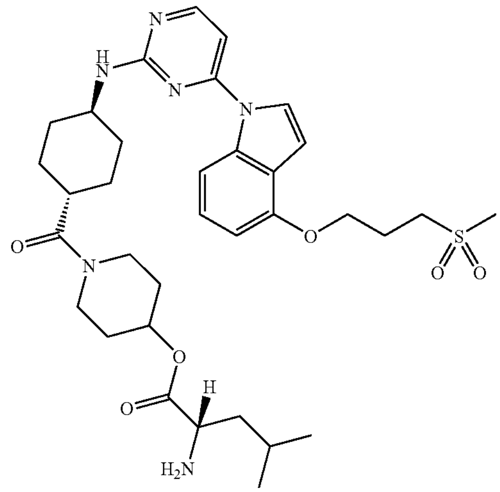 | 153.0-154.0 |
| I-4 | (2S,3S)-2-Amino-3-methyl-pentanoic acid 1-(4-{4-[4-(3-methanesulfonyl-propoxy)-indol-1-yl]-pyrimidin-2-ylamino}-cyclohexanecarbonyl)-piperidin-4-yl ester | 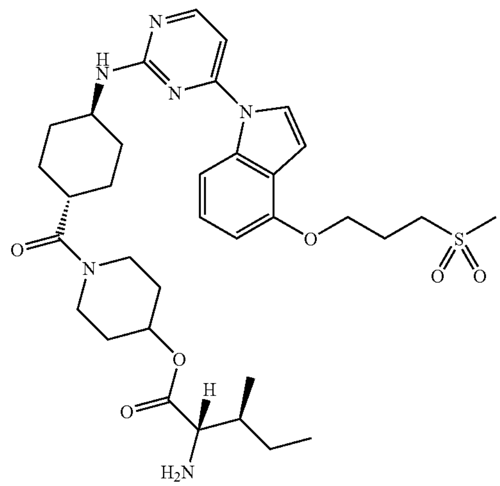 | 137.0-138.0 |
| I-5 | (S)-Pyrrolidine-2-carboxylic acid 1-(4-{4-[4-(3-methanesulfonyl-propoxy)-indol-1-yl]-pyrimidin-2-ylamino}-cyclohexanecarbonyl)-piperidin-4-yl ester | 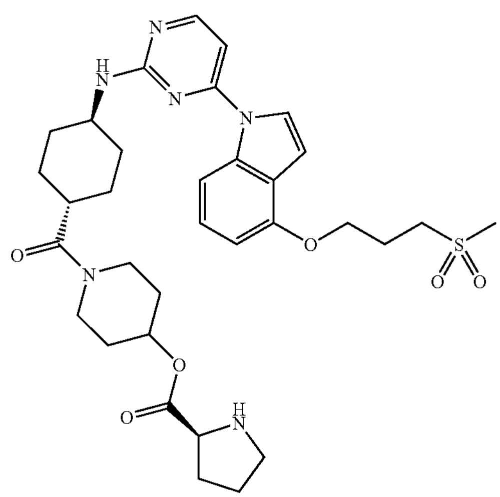 | 147.0-148.0 |

TABLE X-continued

| Compound | Nomenclature | Structure | Melting point |
|---|---|---|---|
| I-6 | (S)-2-Amino-3-methyl-butyric acid 1-(4-{4-[4-(3-methanesulfonyl-propoxy)-indol-1-yl]-pyrimidin-2-ylamino}-cyclohexanecarbonyl)-piperidin-4-yl ester | 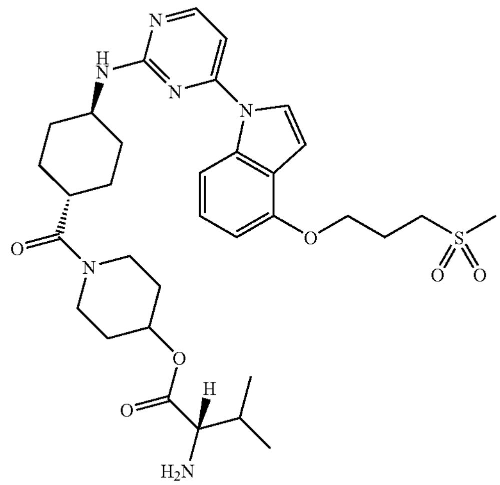 | 163.0-164.0 |
| I-7 | (R)-1-Methyl-pyrrolidine-2-carboxylic acid 1-(4-{4-[4-(3-methanesulfonyl-propoxy)-indol-1-yl]-pyrimidin-2-ylamino}-cyclohexanecarbonyl)-piperidin-4-yl ester | 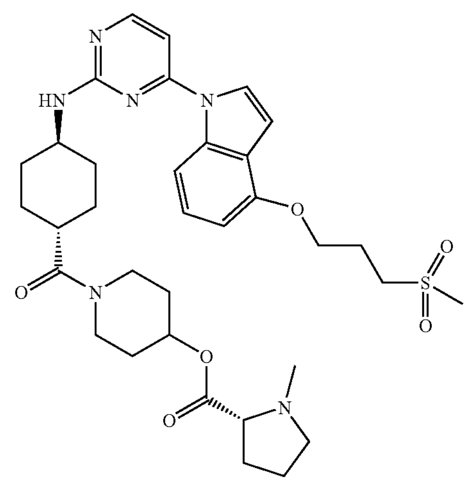 | 127.0-128.0 |
| I-8 | Dimethylamino-acid acid 1-(4-{4-[4-(3-methanesulfonyl-propoxy)-indol-1-yl]-pyrimidin-2-ylamino}-cyclohexanecarbonyl)-piperidin-4-yl ester | 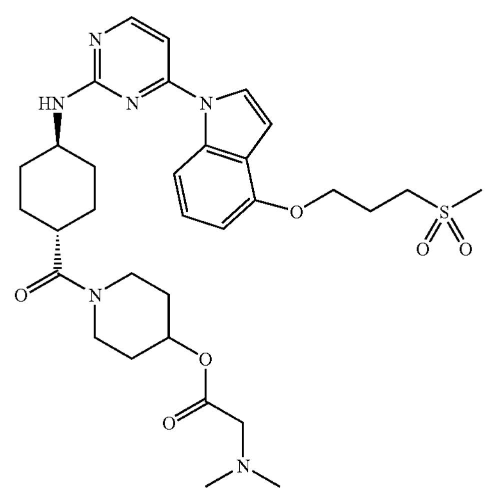 | 177.0-178.0 |

TABLE X-continued

| Compound | Nomenclature | Structure | Melting point |
|---|---|---|---|
| I-9 | (S)-2-methylamino-propionic acid 1-(4-{4-[4-(3-methanesulfonyl-propoxy)-indol-1-yl]-pyrimidin-2-ylamino}-cyclohexanecarbonyl)-piperidin-4-yl ester | 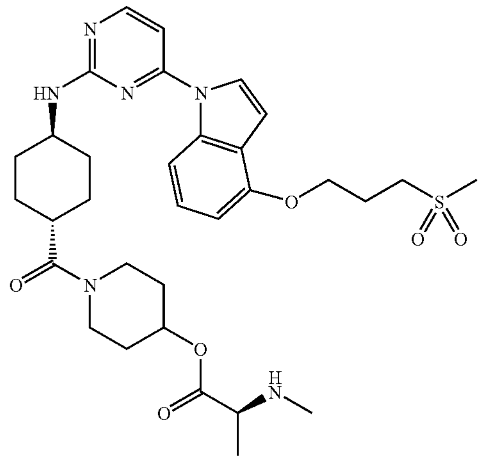 | 182.0-183.0 |
| I-10 | (2R,3S)-2-Amino-3-methyl-pentanoic acid 1-(4-{4-[4-(3-methanesulfonyl-propoxy)-indol-1-yl]-pyrimidin-2-ylamino}-cyclohexanecarbonyl)-piperidin-4-yl ester | 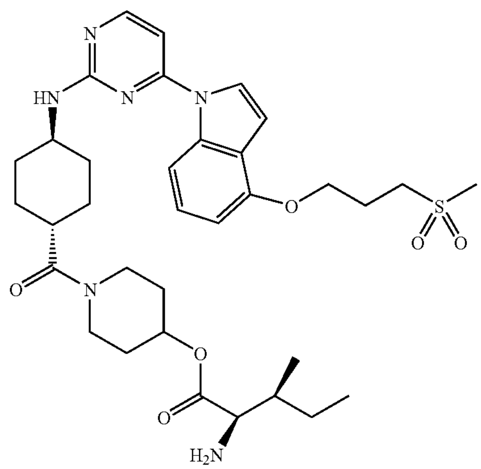 | 150.0-200.0 |
| I-11 | (2R,3R)-2-Amino-3-methyl-pentanoic acid 1-(4-{4-[4-(3-methanesulfonyl-propoxy)-indol-1-yl]-pyrimidin-2-ylamino}-cyclohexanecarbonyl)-piperidin-4-yl ester | 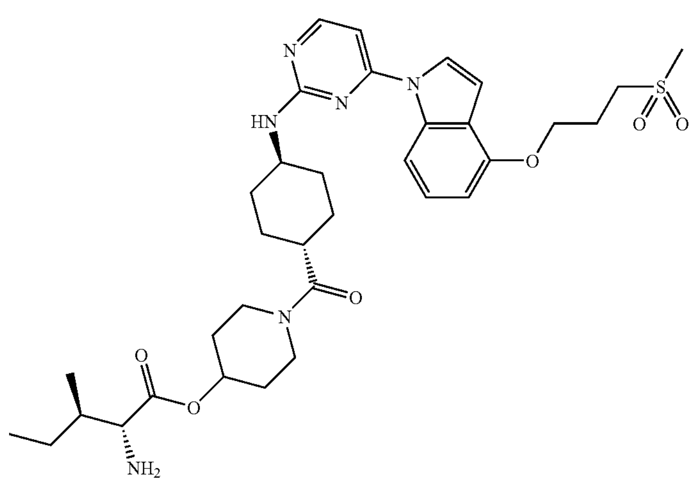 | 147.0-148.0 |

TABLE X-continued

| Compound | Nomenclature | Structure | Melting point |
|---|---|---|---|
| I-12 | Phosphoric acid 1-(4-{4-[4-(3-methanesulfonyl-propoxy)-indol-1-yl]-pyrimidin-2-ylamino}-cyclohexanecarbonyl)-piperidin-4-yl ester dimethyl ester | 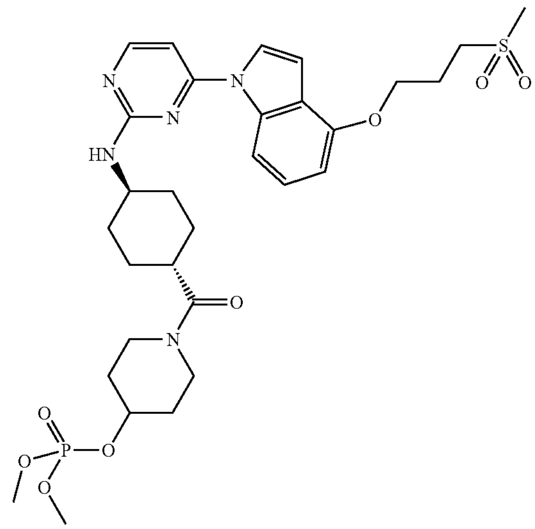 | 135.0-136.0 |
| I-13 | Phosphoric acid mono-[1-(4-{4-[4-(3-methanesulfonyl-propoxy)-indol-1-yl]-pyrimidin-2-ylamino}-cyclohexanecarbonyl)-piperidin-4-yl ester | 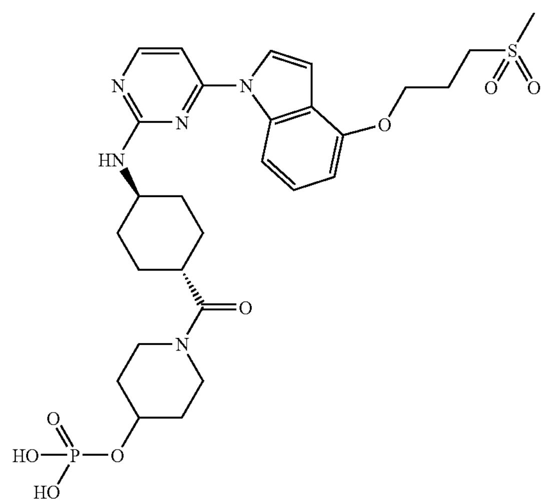 | 201.3-208.8 |
| I-14 | Succinic acid mono-[1-(4-{4-[4-(3-methanesulfonyl-propoxy)-indol-1-yl]-pyrimidin-2-ylamino}-cyclohexanecarbonyl)-piperidin-4-yl ester | 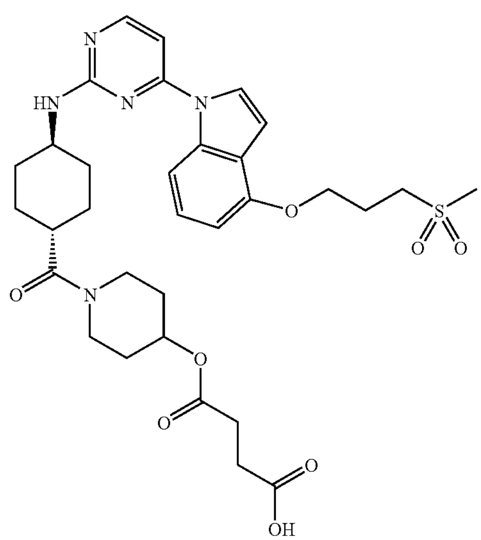 | 214.2-217.7 |

TABLE X-continued

| Compound | Nomenclature | Structure | Melting point |
|---|---|---|---|
| I-15 | (R)-3-Methyl-2-methylamino-butyric acid 1-(4-{4-[4-(3-methanesulfonyl-propoxy)-indol-1-yl]-pyrimidin-2-ylamino}-cyclohexanecarbonyl)-piperidin-4-yl ester | 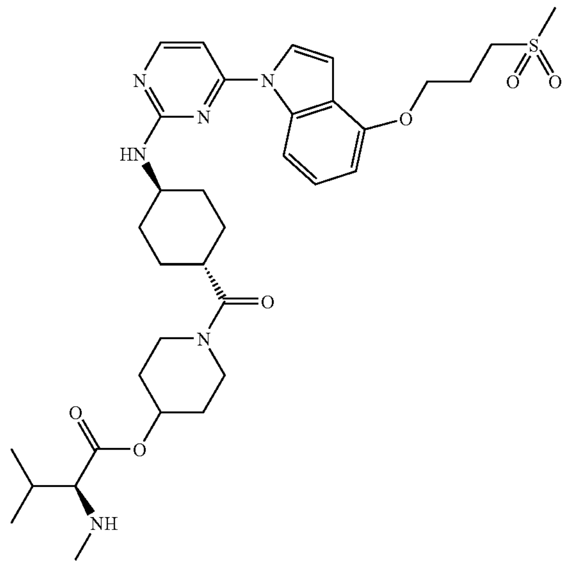 | 105.0-107.0 |
| I-16 | (2R,3R)-3-Methyl-2-methylamino-pentanoic acid 1-(4-{4-[4-(3-methanesulfonyl-propoxy)-indol-1-yl]-pyrimidin-2-ylamino}-cyclohexanecarbonyl)-piperidin-4-yl ester | 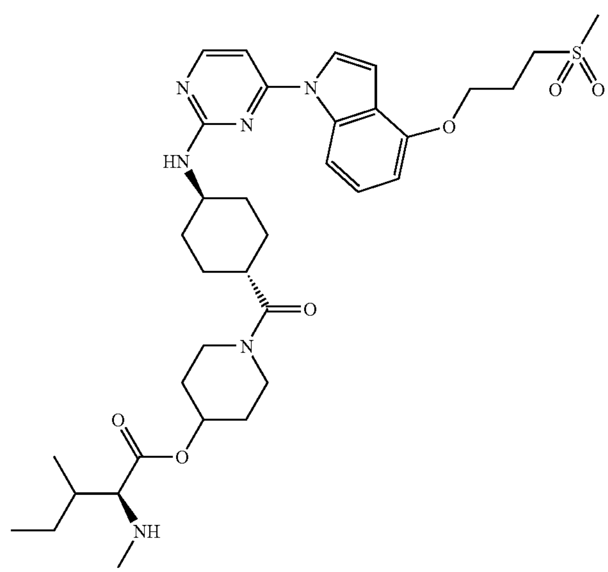 | |

TABLE X-continued

| Compound | Nomenclature | Structure | Melting point |
|---|---|---|---|
| I-17 | (S)-1-Ethyl-pyrrolidine-2-carboxylic acid 1-(4-{4-[4-(3-methanesulfonyl-propoxy)-indol-1-yl]-pyrimidin-2-ylamino}-cyclohexanecarbonyl)-piperidin-4-yl ester | 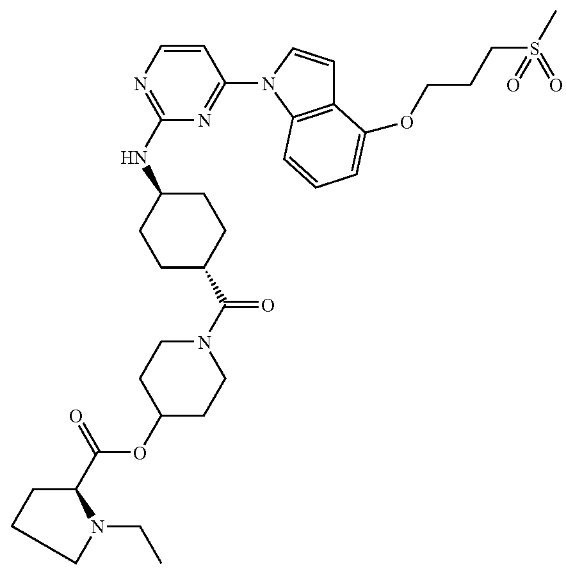 | |
| I-18 | 1-Methylamino-cyclopropanecarboxylic acid 1-(4-{4-[4-(3-methanesulfonyl-propoxy)-indol-1-yl]-pyrimidin-2-ylamino}-cyclohexanecarbonyl)-piperidin-4-yl ester | 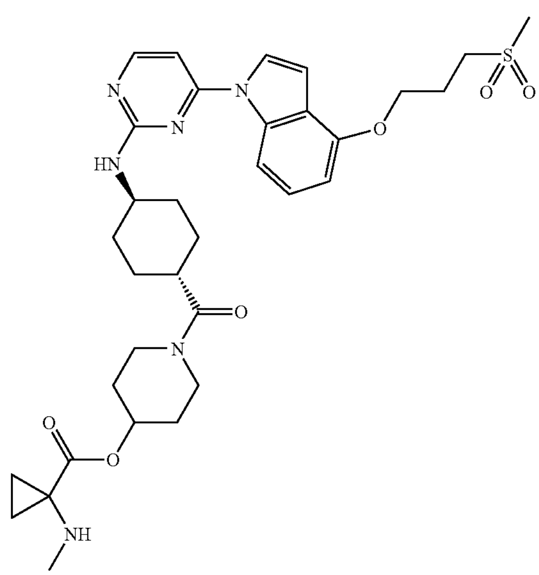 | |

TABLE X-continued

| Compound | Nomenclature | Structure | Melting point |
|---|---|---|---|
| I-19 | (S)-1-Methyl-piperidine-2-carboxylic acid 1-(4-{4-[4-(3-methanesulfonyl-propoxy)-indol-1-yl]-pyrimidin-2-ylamino}-cyclohexanecarbonyl)-piperidin-4-yl ester | 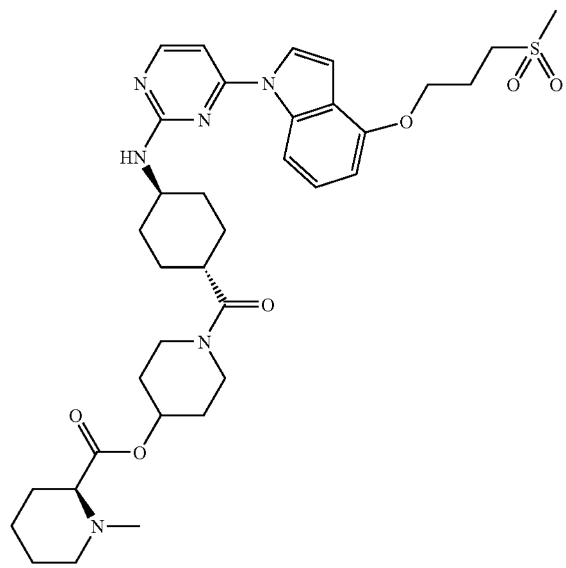 | |
| I-20 | 3-Amino-propionic acid 1-(4-{4-[4-(3-methanesulfonyl-propoxy)-indol-1-yl]-pyrimidin-2-ylamino}-cyclohexanecarbonyl)-piperidin-4-yl ester | 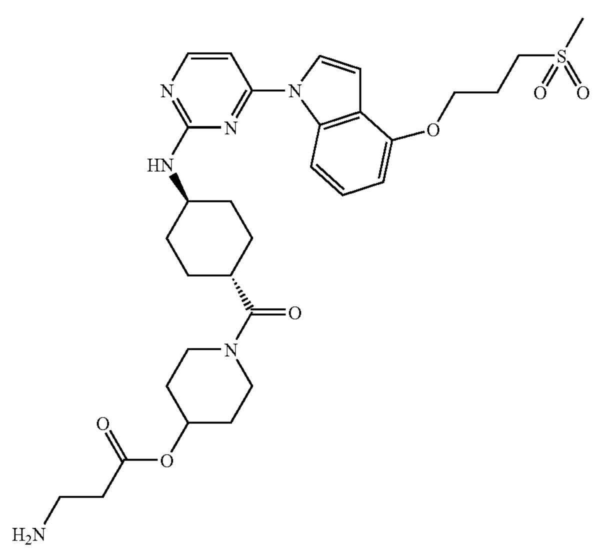 | |

TABLE X-continued

| Compound | Nomenclature | Structure | Melting point |
|---|---|---|---|
| I-21 | 3-Dimethylamino-propionic acid 1-(4-{4-[4-(3-methanesulfonyl-propoxy)-indol-1-yl]-pyrimidin-2-ylamino}-cyclohexanecarbonyl)-piperidin-4-yl ester | 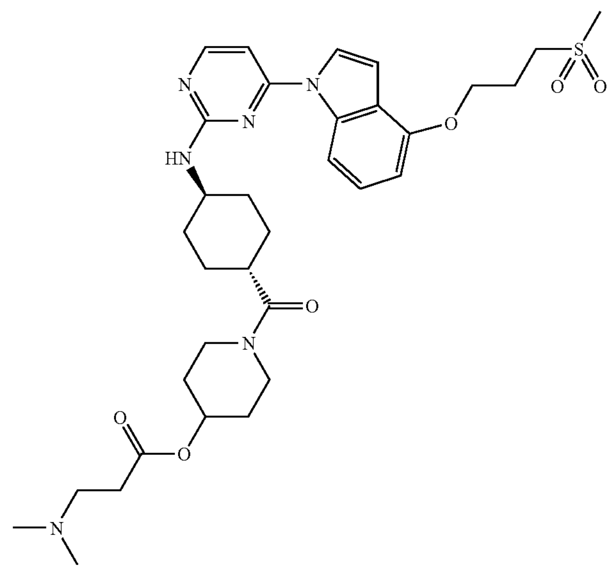 | |
| I-22 | Trimethylammoinium-propionic acid 1-(4-{4-[4-(3-methanesulfonyl-propoxy)-indol-1-yl]-pyrimidin-2-ylamino}-cyclohexanecarbonyl)-piperidin-4-yl ester | 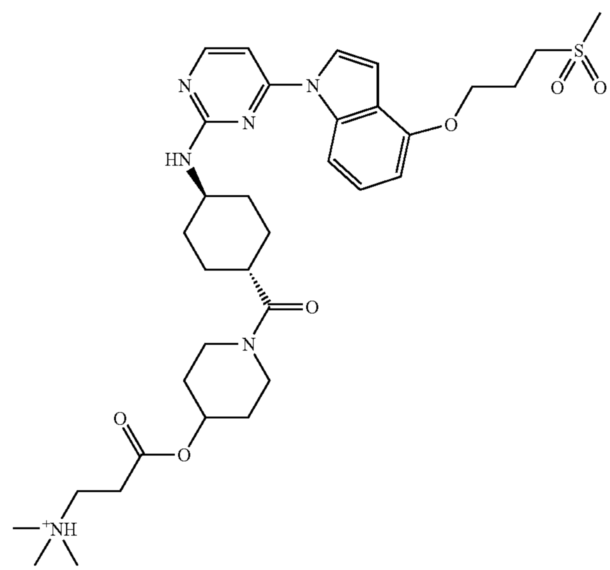 | |
| I-23 | Amino-acetic acid 1-(4-{4-[4-(3-methanesulfonyl-propoxy)-indol-1-yl]-pyrimidin-2-ylamino}-cyclohexanecarbonyl)-piperidin-4-yl ester | 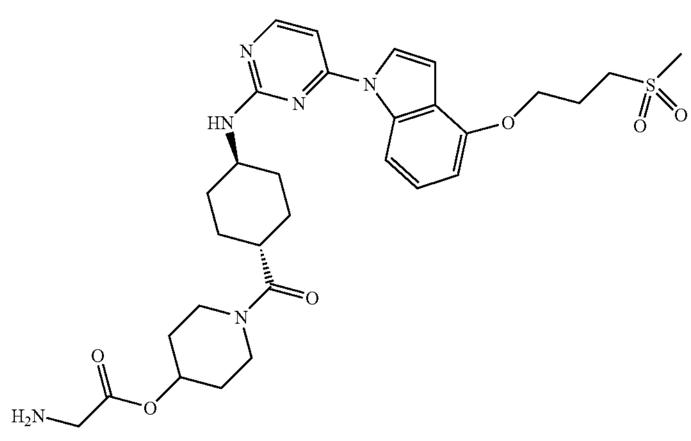 | |

TABLE X-continued

| Compound | Nomenclature | Structure | Melting point |
|---|---|---|---|
| I-24 | Methylamino-acetic acid 1-(4-{4-[4-(3-methanesulfonyl-propoxy)-indol-1-yl]-pyrimidin-2-ylamino}-cyclohexanecarbonyl)-piperidin-4-yl ester | 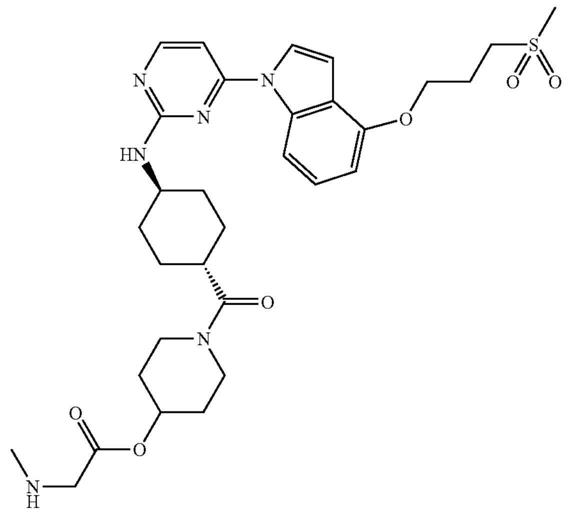 | |
| I-25 | Propionic acid 1-(4-{4-[4-(3-methanesulfonyl-propoxy)-indol-1-yl]-pyrimidin-2-ylamino}-cyclohexanecarbonyl)-piperidin-4-yl ester | 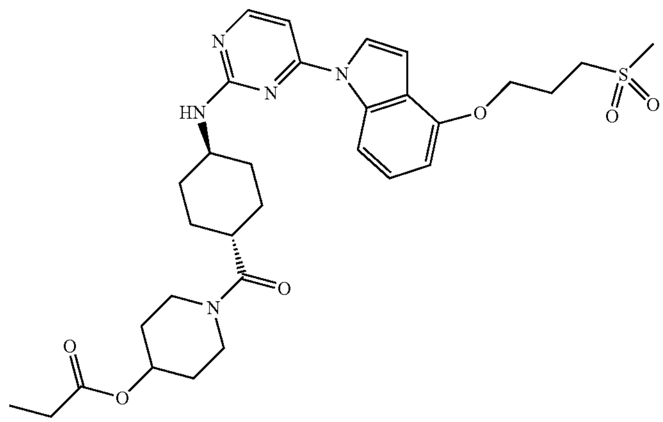 | |
| I-26 | (S)-4-Hydroxy-1-methyl-pyrrolidine-2-carboxylic acid 1-(4-{4-[4-(3-methanesulfonyl-propoxy)-indol-1-yl]-pyrimidin-2-ylamino}-cyclohexanecarbonyl)-piperidin-4-yl ester | 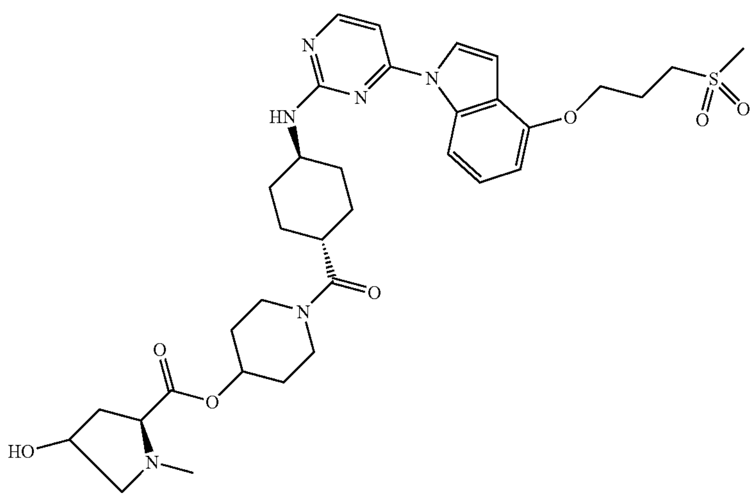 | |

TABLE X-continued

| Compound | Nomenclature | Structure | Melting point |
|---|---|---|---|
| I-27 | (S)-1-Methyl-pyrrolidine-2-carboxylic acid 1-(4-{4-[4-(3-methanesulfonyl-propoxy)-indol-1-yl]-pyrimidin-2-ylamino}-cyclohexanecarbonyl)-piperidin-4-yl ester | 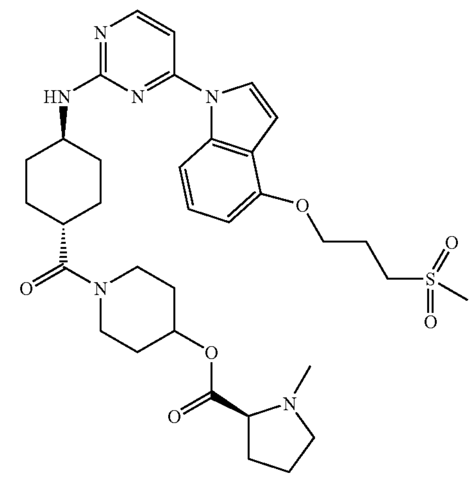 | 127.0-128.0 |
| I-28 | Acetic acid 1-(4-{4-[4-(3-methanesulfonyl-propoxy)-indol-1-yl]-pyrimidin-2-ylamino}-cyclohexanecarbonyl)-piperidin-4-yl ester | 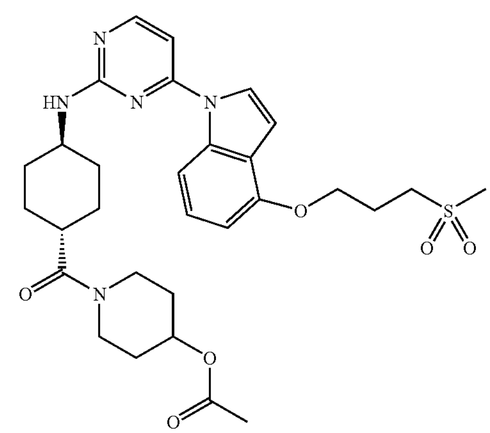 | |
| I-29 | Nicotinic acid 1-(4-{4-[4-(3-methanesulfonyl-propoxy)-indol-1-yl]-pyrimidin-2-ylamino}-cyclohexanecarbonyl)-piperidin-4-yl ester | 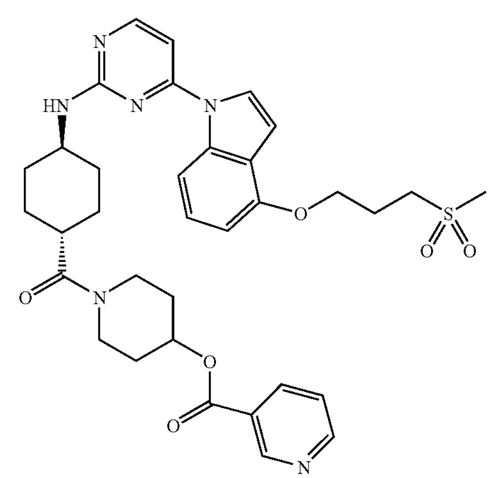 | |

TABLE X-continued

| Compound | Nomenclature | Structure | Melting point |
|---|---|---|---|
| I-30 | (2R,3R)-2-(tert-Butoxycarbonyl)-methyl-amino)-3-methyl-pentanoic acid 1(4-{4-[4-(3-methanesulfonyl-propoxy)-indol-1-yl]-pyrimidin-2-ylamino}-cyclohexanecarbonyl) piperidin-4-yl ester | 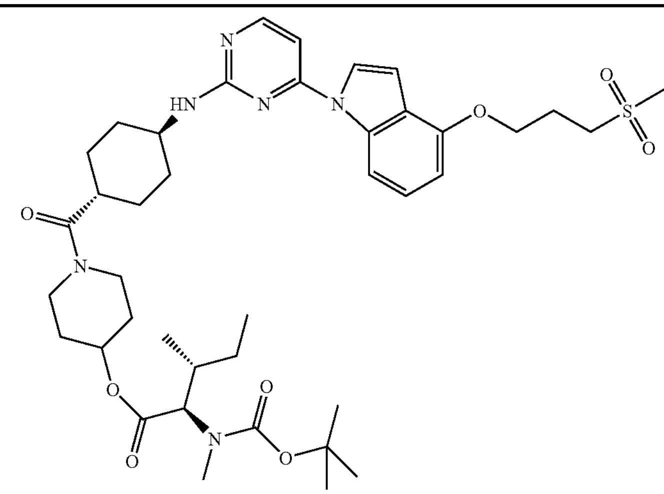 | |
| I-31 | (R)-2-(tert-Butoxycarbonyl-methyl-amino)-3-methyl-butyric acid 1-(4-{4-[4-(3-methanesulfonyl-propoxy)-indol-1-yl]-pyrimidin-2-ylamino}-cyclohexanecarbonyl)-piperidin-4-yl ester | 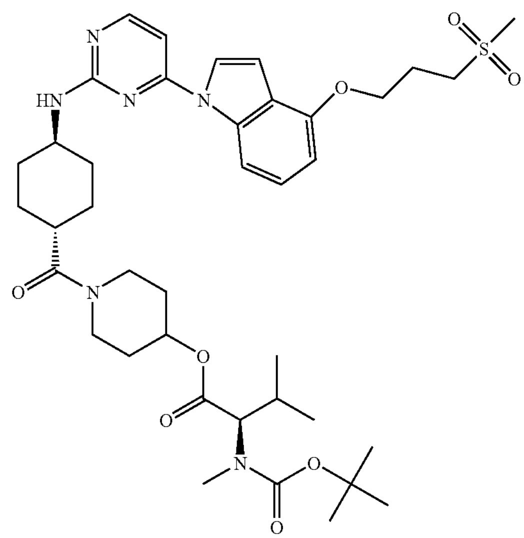 | |

Utility

The compounds of this invention are JNK modulators and as such are expected to be effective in the treatment of a wide range of JNK mediated disorders. Exemplary JNK mediated disorders include, but are not limited to, autoimmune disorders, inflammatory disorders, metabolic disorders, neurological disease, and cancer. Accordingly, compounds of the invention can be used to treat one or more of such disorders. In some embodiments, compounds of the invention can be used to treat a JNK mediated disorder such as rheumatoid arthritis, asthma, type II diabetes, Alzheimer's disease, Parkinson's disease or stroke.

Administration and Pharmaceutical Compositions

The invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use.

Formulations containing about one (1) mg of active ingredient or, more broadly, about 0.01 to about one hundred (100) mg, per tablet, are accordingly suitable representative unit dosage forms.

The compounds of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the invention may also be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described below.

Additional objects, advantages, and novel features of this invention will become apparent to those skilled in the art upon examination of the following examples thereof, which are not intended to be limiting.

LIST OF ABBREVIATIONS

Ac₂O Acetic anhydride
AcOH Acetic acid
DBU 1,8-Diazabicyclo[5.4.0]undec-7-ene
DCE 1,2-Dichloroethane
DCM Dichloromethane/Methylene chloride
DIPEA Diisopropylethylamine
DMF N,N-dimethylformamide
DMSO Dimethyl sulfoxide
EDCI 1-(3-Dimethylaminopropyl)-3-ethylcarbodiimide hydrochloride
Et₂O Diethyl ether
EtOH Ethanol/Ethyl alcohol
EtOAc Ethyl acetate
HOBt 1-Hydroxybenzotriazole
LDA Lithium diisopropylamide
LiHMDS Lithium bis(trimethylsilyl)amide m-CPBA 3-Chloroperoxybenzoic acid
MeOH Methanol/Methyl alcohol
MW Microwaves
NMP 1-Methyl-2-pyrrolidinone
PMB 4-Methoxy benzyl
RT Room temperature
TBME tert-Butyl methyl ether
TFA Trifluoroacetic acid
Tf₂O Trifluoromethanesulfonic anhydride
THF Tetrahydrofuran
TLC Thin layer chromatography

EXAMPLES

The following preparations and examples are given to enable those skilled in the art to more clearly understand and to practice the present invention. They should not be considered as limiting the scope of the invention, but merely as being illustrative and representative thereof.

Example 1

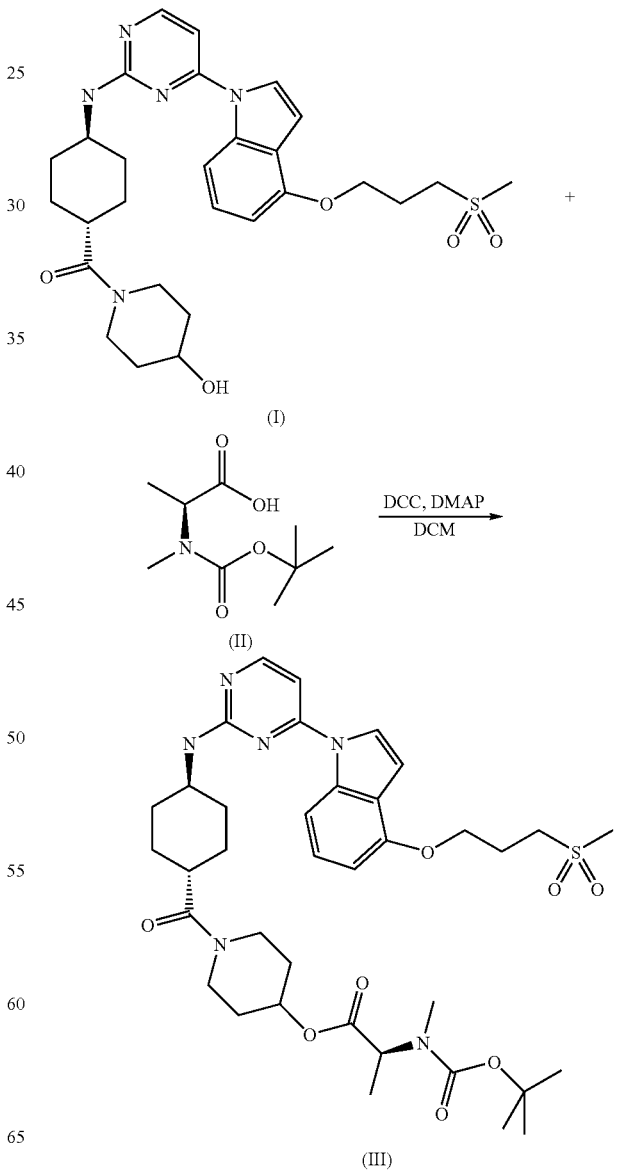

To a suspension of 1.0 mMol (0.556 g) I in 20 mL DCM, 5.0 mMol (1.032 g) DCC and 3.0 mMol (0.367 g) DMAP were added, and stirred at r.t. for 5 minutes under N₂. 2.0 mMol (0.406 g) II was then added and stirred at r.t. for 1 h. The reaction mixture was then diluted with DCM, washed with H₂O (×4) and brine. The organic layer was then dried with Na₂SO₄, filtered, and solvent removed in vacuo. The residue was purified on a silica gel column (1.5-5%, MeOH-DCM), and the solvent removed to yield 0.656 g III as the free base ([M+1] 741).

Example 2

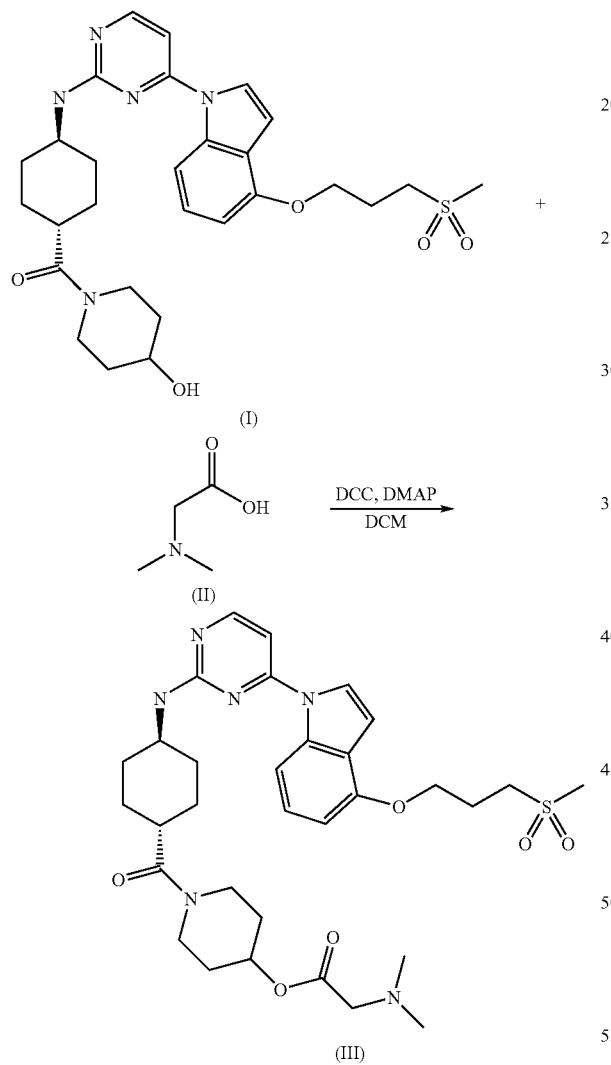

To a suspension of 1.0 mMol (0.556 g) I in 20 mL DCM, 5.0 mMol (1.032 g) DCC and 3.0 mMol (0.367 g) DMAP were added, and stirred at r.t. for 5 minutes under N₂. 2.0 mMol (0.206 g) II was then added and stirred at r.t. overnight. The reaction mixture was then diluted with DCM, washed with H₂O (×4) and brine. The organic layer was then dried with Na₂SO₄, filtered, and solvent removed in vacuo. The residue was purified on a silica gel column (2.0-6.5%, MeOH-DCM+0.1% NH₄OH), and the solvent removed to yield 0.398 g III as the free base. 157 mg III was then dissolved in EtOAc with a few drops of EtOH, on a steam bath and allowed to cool to r.t., and 10% ethanolic HCl was added. After concentrating, the solution was stirred into Et₂O to yield III, a light yellow precipitate as the HCl salt.

Example 3

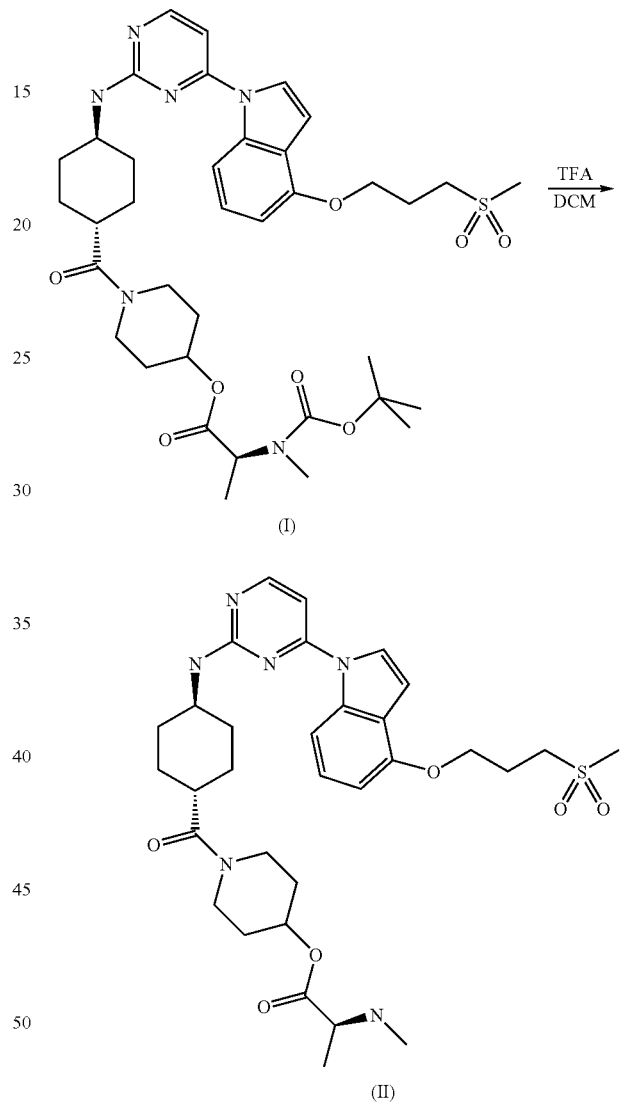

To a solution of 0.656 g I in 1 mL DCM on an ice bath was added 1 mL TFA and allowed to stir for 1 hour on ice and subsequently several hours at r.t. The mixture was purified on a silica gel column (2.5-10% MeOH-DCM+0.1% NH₄OH), stirred in EtOAc-hexane, the resultant solid filtered off and dried in vacuo at 50° C. to yield 0.265 g II (MP: 182-183° C., M+1: 641). 148 mg II was dissolved in heated EtOH and 10% ethanolic HCl was then added. Upon addition of Et₂O, a light yellow precipitate formed, was allowed to stir overnight, and the solid filtered under N₂ and dried in vacuo at 50° C. (158 mg HCl salt of II).

Example 4

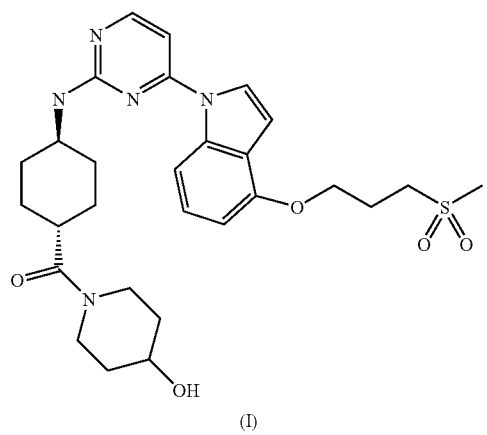

Example 5

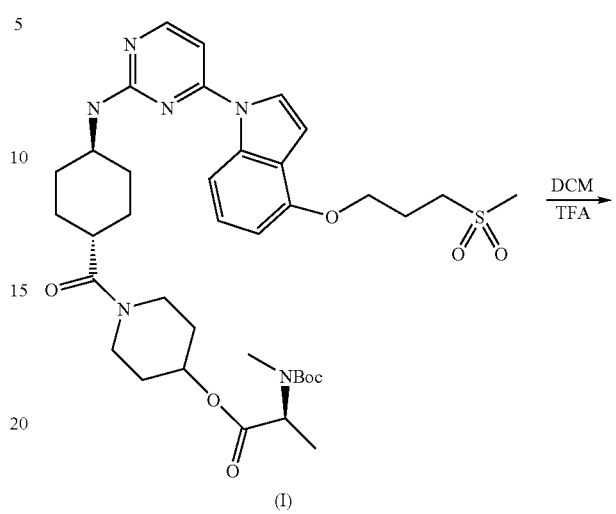

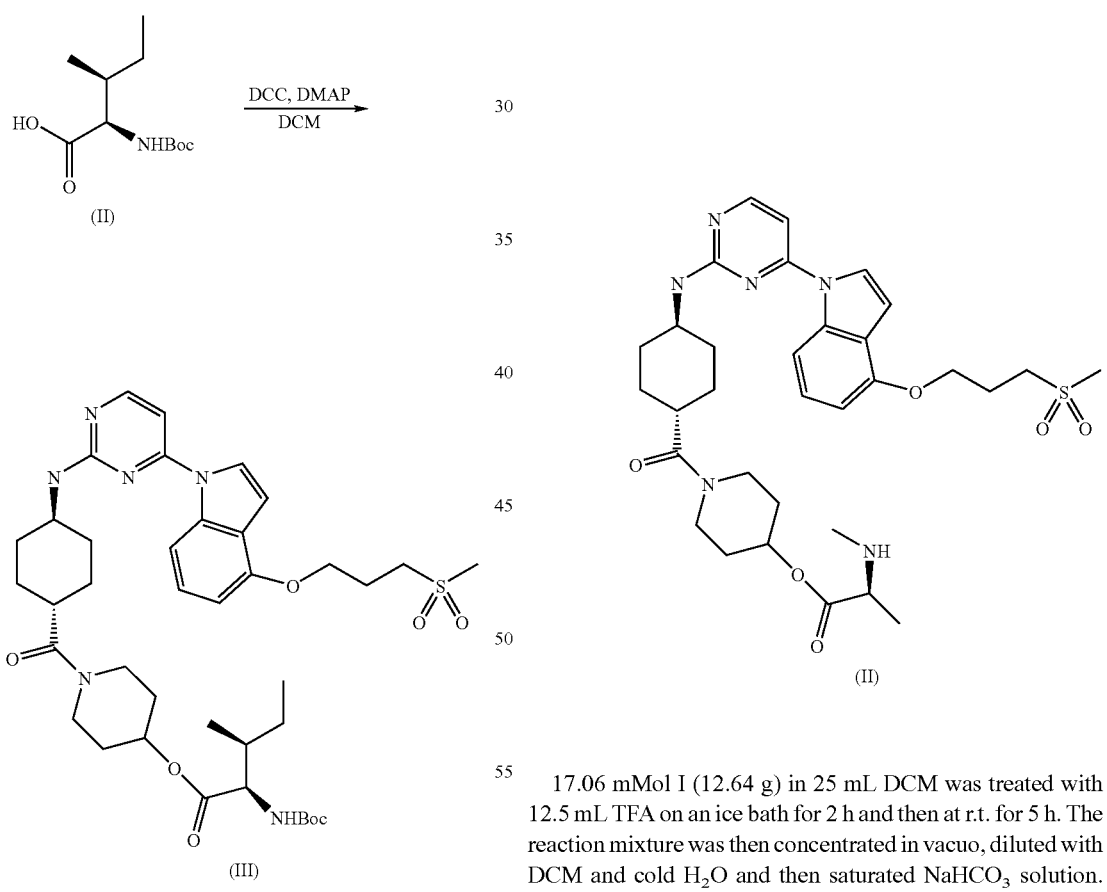

A mixture of 9.105 mMol I (5.06 g), 13.66 mMol II (3.16 g), 18.21 mMol DCC (3.76 g), and 13.66 mMol DMAP (1.67 g) were stirred in 100 mL DCM at r.t. under $N_2$ overnight. The mixture was purified on a silica gel column (2-5% MeOH-DCM) to yield III as a fine white powder (84%).

17.06 mMol I (12.64 g) in 25 mL DCM was treated with 12.5 mL TFA on an ice bath for 2 h and then at r.t. for 5 h. The reaction mixture was then concentrated in vacuo, diluted with DCM and cold $H_2O$ and then saturated $NaHCO_3$ solution. The organic later was separated and the aqueous layer extracted with DCM (×4). The combined organic layers were washed with $H_2O$ and brine, dried with $Na_2SO_4$, filtered and solvent removed in vacuo. The product was then purified on a silica gel column (3-10% MeOH-DCM) and the product stirred in EtOAc and dried at 70 C to yield II (MP: 184.1-185.8° C.).

Example 6

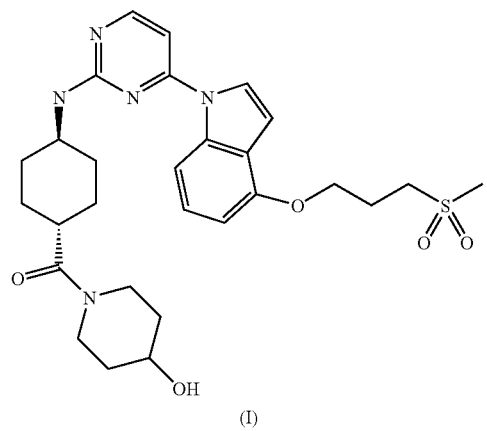

(I)

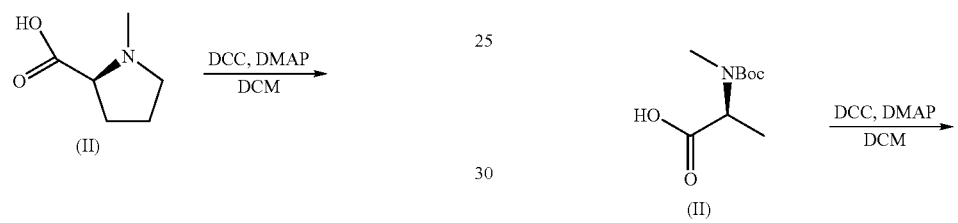

(II)

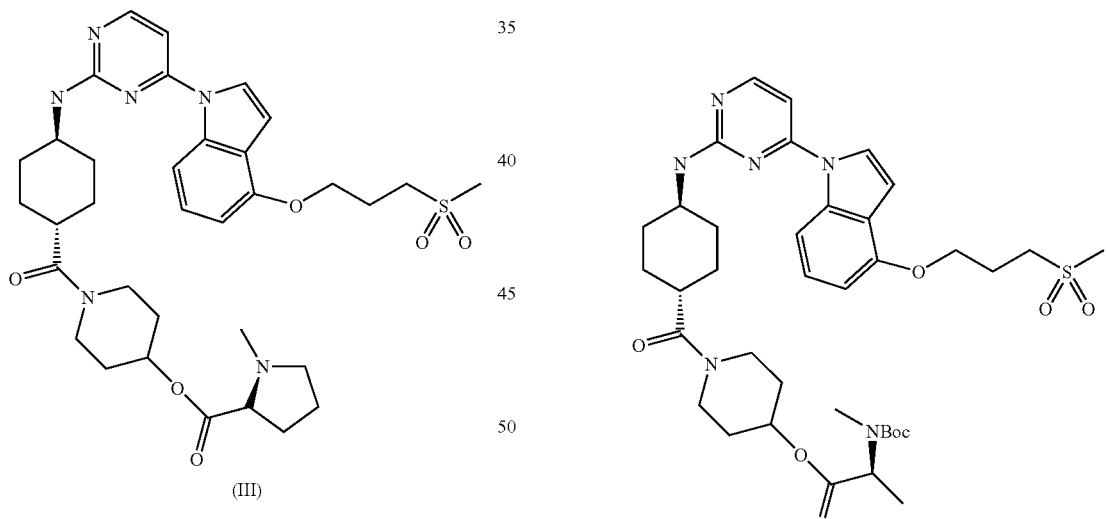

(III)

A mixture of 18.6 mMol I (10.33 g), 38.7 mMol II (5.0 g), 37.2 mMol DCC (7.67 g), and 27.9 mMol DMAP (3.41 g) were stirred in 150 mL dry DCM under $N_2$ at r.t. overnight. $Et_3N$ (5.4 mL) was then added as well as 7.5 g DCC and 3.4 g DMAP and stirred at r.t. overnight. 1 g DCC and 1.5 g DMAP then added and stirred for 2 days at r.t. The mixture was filtered and the filtrate washed with $H_2O$ (×4) and brine, dried with $Na_2SO_4$, filtered, and the solvent removed in vacuo. The product was purified on a silica gel column (2-8% MeOH-DCM). The white solid obtained was then heated in boiling EtOAc and filtered hot, to yield 10.769 g III (86.8%) (MP: 128-130° C.).

Example 7

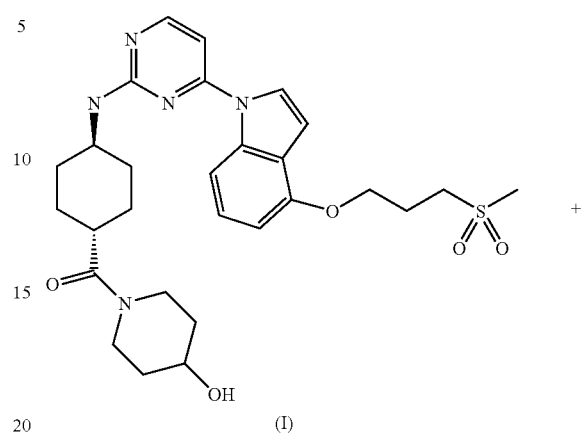

(I)

(II)

(III)

A mixture of 18 mMol I (10 g), 27 mMol II (5.49 g), 36 mMol DCC (7.42 g), and 27 mMol DMAP (3.3 g) in 150 mL DCM were stirred at r.t. under $N_2$ overnight. The reaction mixture was then filtered and the residue washed with DCM and filtered. The combined DCM filtrates were then washed with $H_2O$ (×3) and brine. The organic layer was then dried with $Na_2SO_4$, filtered, and the solvent removed in vacuo. The residue was purified on a silica gel column (2-8% MeOH-DCM) to give III (95%) (M+1: 741).

Example 8

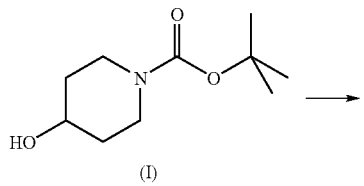

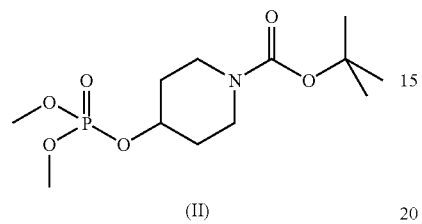

A solution of tert-butyl-4-hydroxy-1-piperidine carboxylate 1 (2.00 g, 10 mmol) and tetrabromomethane (6.60 g, 20 mmol) in 12 mL of pyridine was degassed by bubbling nitrogen via syringe for 10 min., cooled in an ice bath and slowly added trimethyl phosphite (2.50 mL, 21 mmol)—precipitate formed immediately then a yellow color slowly formed, continued stirring at 0° C. for 30 min., then at room temp for 1.5 hrs., the dark-yellow/orange reaction mixture was partitioned between aq. HCl and EtOAc, the organic layer was washed twice more with 1N HCl, dried over $Na_2SO_4$, filtered, concentrated, loaded onto silica gel and purified by flash chromatography (1:1 EtOAc/hexanes then 100% EtOAc) and dried to give a light-yellow liquid which crystallized on standing to give the product II as an off-white solid (2.01 g, 65%, mp=80-82° C.).

Example 9

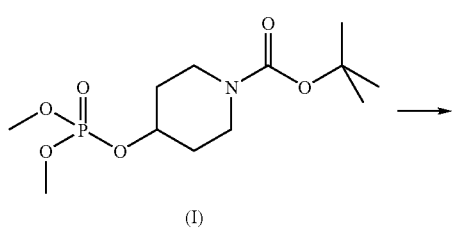

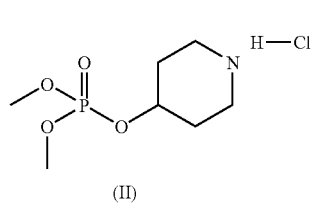

To a solution of the BOC-piperidine 1 (2.01 g, 6.5 mmol) in 20 mL of methanol, was added 6 mL of a 4M solution of HCl in dioxane (24 mmol) and stirred at RT for 16 hrs, concentrated to give a brown liquid which slowly congealed on standing to give the product II as pasty light-brown material (1.64 g, ca. 100%).

Example 10

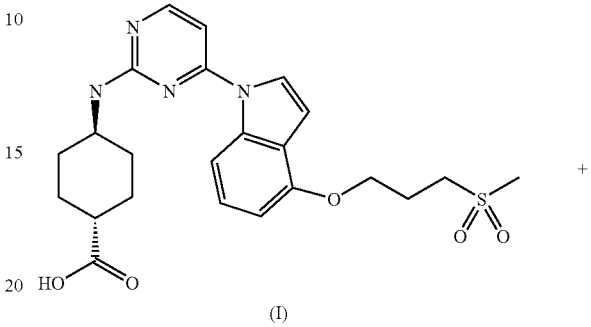

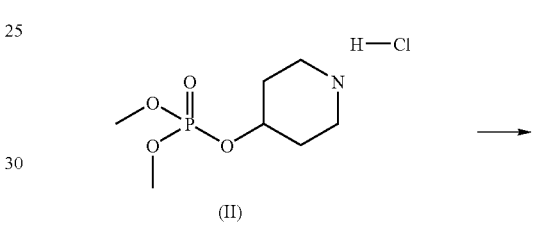

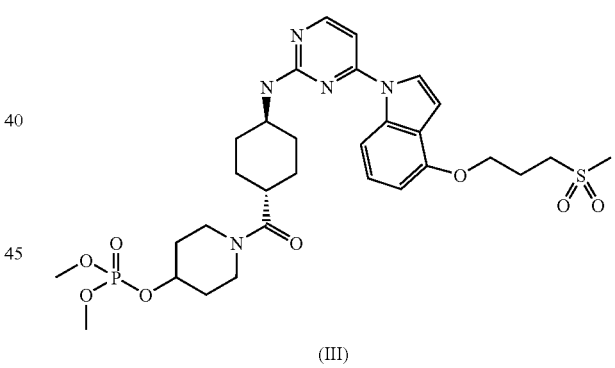

A mixture of the acid I (2.59 g, 5 mmol), II (1.64 g, 7 mmol), benzotriazol-1-yloxytris(dimethylamino)phosphonium hexafluorophosphate, BOP (3.60 g, 8 mmol), N,N-diisopropyl ethyl amine (4 mL, 23 mmol) in 75 mL of THF (low solubility) and 50 mL of NMP were stirred at RT under nitrogen for 23 hrs, concentrated, then partitioned between water and EtOAc (product oils out of EtOAc solution), washed with water, dried over $Na_2SO_4$, filtered, concentrated, loaded onto silica gel and attempted to purify by flash chromatography (3:97 MeOH/$CH_2Cl_2$), but impurities co-eluted, so starting material was removed by washing with aq. NaOH soln (emulsion formed), then dilute HCl soln, re-purified by flash chromatography (3:97-5:95 MeOH/$CH_2Cl_2$) then dried to give the product III as a white foam (645 mg, 18%, mp=125-126° C.).

Example 11

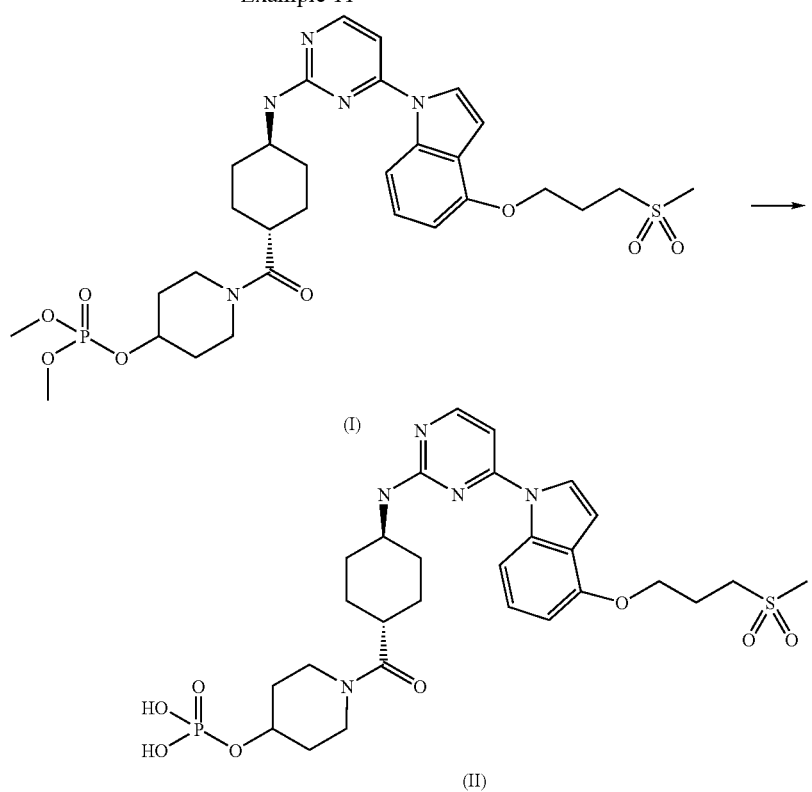

To a 0° C. solution of the phosphate ester I (871 mg, 1.3 mmol) in 50 mL of $CH_2Cl_2$ was added trimethylsilyl bromide via syringe (0.70 mL, 5.2 mmol)—precipitate formed immediately, but became homogeneous after stirring. The reaction mixture was stirred for 5 hrs., allowing to slowly warm to RT, still contains trace SM, so added an additional 0.2 mL of TMSBr and stirred for 1 hr., cooled to 0° C. and quenched with MeOH, stirred for 20 min., then concentrated to give a yellow crude solid. The crude solids were dissolved in 1M NaOH soln and washed with 3 portions of EtOAc, neutralized with 1N HCl soln and brought pH to about 3, the gummy yellow suspension was filtered, the solids were washed with water, then taken up into $CH_2Cl_2$/MeOH, concentrated and triturated with EtOAc, the suspension was filtered and washed with EtOAc and dried overnight in a 50° C. vacuum oven to give the product II as a pale-yellow powder (667 mg, 80%, mp=201.3-208.8° C.).

Example 12

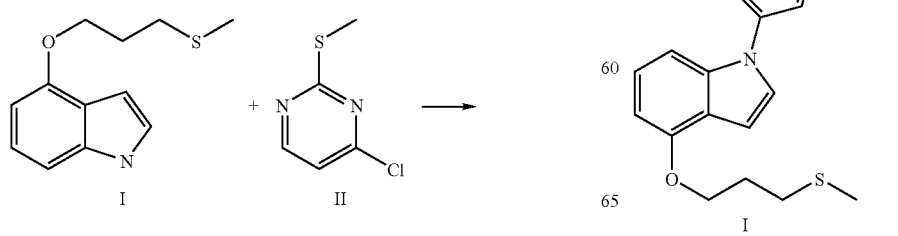

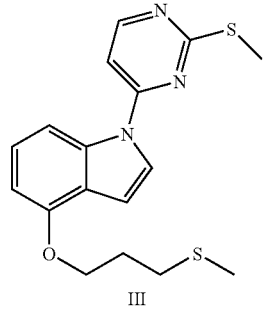

Indole I (400.88 g) in 250 mL THF, 2 L of 1N K$^t$BuO, and 381 g pyrimidine II in 350 mL THF were combined with cooling to maintain under 40° C. and allowed to stir at r.t., for 1 hour. The solvent was then removed in vacuo and the solid was suspended in MeOH, filtered, washed with MeOH, water, and again with MeOH, to yield 87.56% III.

Example 13

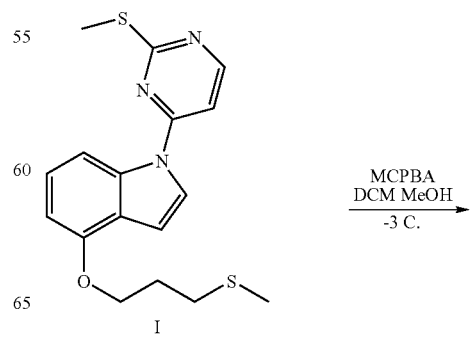

-continued

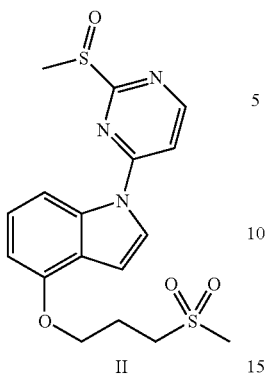

MCPBA (204.3 g, 77%) in DCM (310 mL) and MeOH (155 mL) was added dropwise to 100.0 g I in DCM (590 mL) and methanol (145 ml) at −5° C. over 1.5 h. Additional MCPBA (12.0 g) was added at 2° C. and the reaction mixture diluted after 20 minutes with 900 mL MTBE added slowly over 20 min at 12° C. and allowed to stir for 1.5 h at 20-22° C. MTBE (300 mL) was then added and the mixture filtered after 20 min, the solid rinsed with MTBE (2×200 mL), and the solvent removed in vacuo to yield II (90.2%).

Example 14

550 g II and 815 mL DIPEA were added to 746.7 g I in 2.5 L DMA and the mixture allowed to heat to 120° C. for 4 h and allowed to cool to r.t. 3 L H₂O was added dropwise and the solid filtered, washed with H₂O and MeOH. The solid was then dried in vacuo at 48° C. overnight to yield III (90%).

Example 15

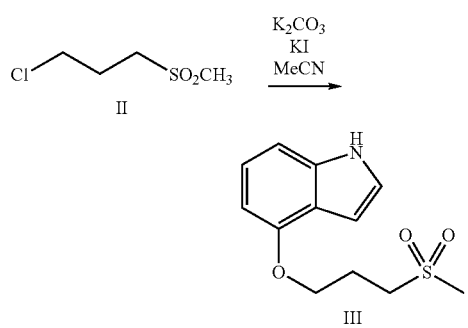

160 g II was added to 108.77 g I, in 1 L MeCN and 338 g K₂CO₃ and 13.36 g KI were added and the reaction mixture stirred overnight at 80° C. After cooling, the mixture was filtered through celite to remove the salts which were rinsed with MeCN and the filtrate vacuum distilled and solvent replaced with DCM (700 mL), filtered, and the solvent removed in vacuo and replaced with MeOH (600 mL). The solvent was partially removed in vacuo at 40° C. and crystallization occurred. After cooling, additional MeOH was added and the slurry was filtered, the solid rinsed with cold MeOH, and the product III (82%) was dried overnight at 35° C. in vacuo under N₂.

Example 16

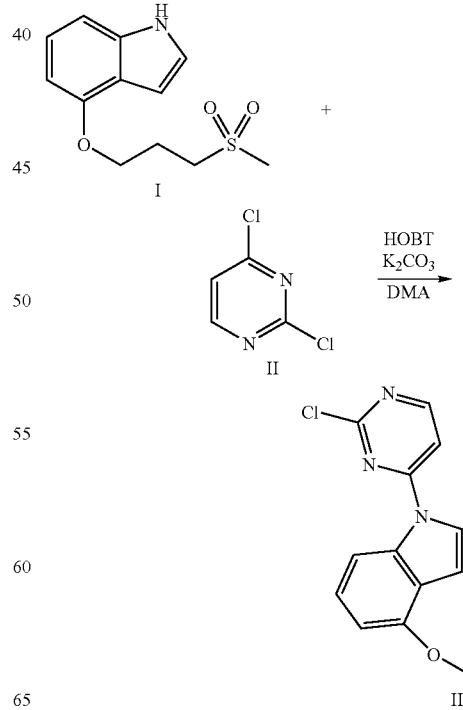

188.1 g I, 221.25 g II, 20.08 g HOBT, 143.68 K$_2$CO$_3$ and DMA (1.6 L) heated to 85° C. for 20 h. 5 L IPA was then added and stirred for 20 min. and cooled to 0° C. for 3 h and the solution filtered, the solid rinsed with IPA (2×300 mL), and deionized H2O (2×1 L), and the solvents removed from the solid in vacuo at 55° C. for 4 days to yield III (94%).

Example 17

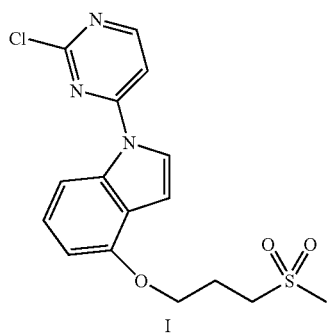

I

+

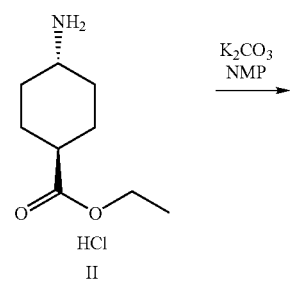

II

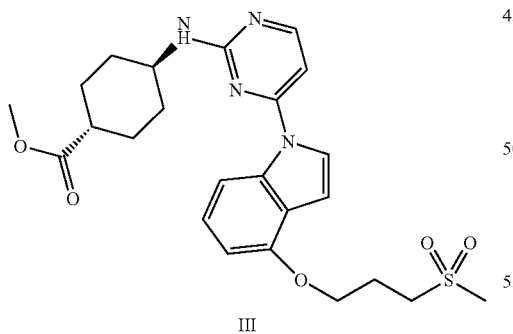

III 300 g I, 155 g II, 170 g K$_2$CO$_3$ in NMP (2.35 L) were stirred at 80° C. for 5 h and allowed to stir overnight at r.t. The reaction mixture was allowed to stir on an ice bath, 2.5 L water was slowly added while stirring, and cooling continued until completion of the exothermic reaction. Upon the reaction mixture cooling to r.t., the mixture was filtered, the solid rinsed with H$_2$O (2×500 mL), and the solid dried in vacuo overnight to yield III (97%).

Example 18

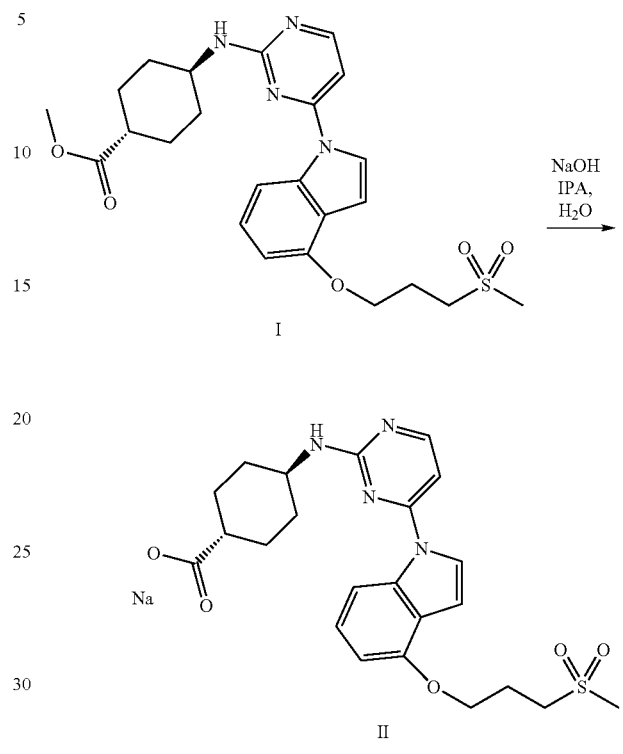

198.95 g of a 50% (w/w) aqueous solution of NaOH in 1660 mL H$_2$O was added to 830.0 g I in 7470 mL IPA and the mixture allowed to stir at 82° C. for 1 h and allowed to stir overnight at r.t. The mixture was then filtered, the solid rinsed with 1 L IPA, and dried in vacuo at 60° C. for 3 days to yield II (96.9%).

Example 19

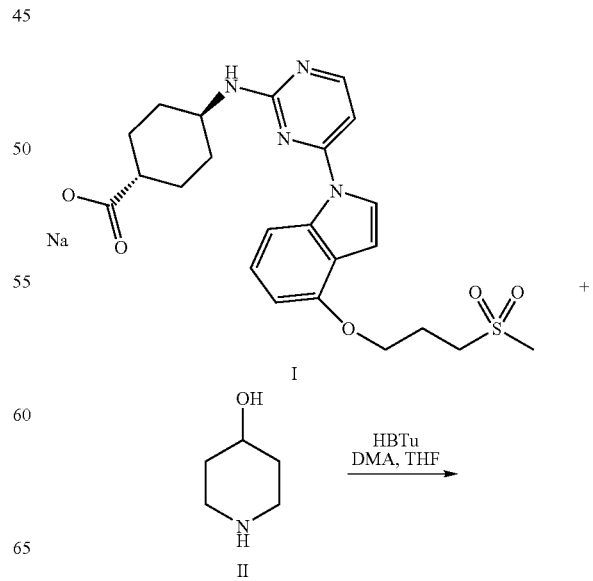

-continued

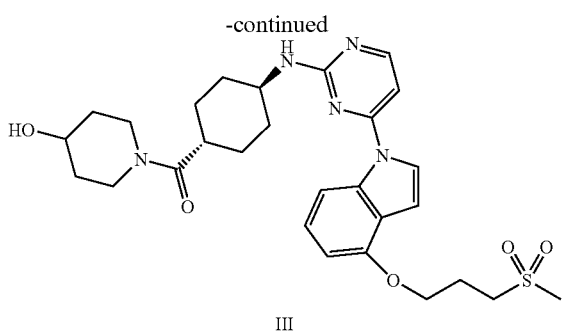

III 1000 g I and 960 g HBTU and 255 g II in 550 mL DMA and 3600 mL THF were allowed to stir for 0.5 h and 140 mL TEA added and allowed to continue stirring at r.t for 3 h. 10 L NaHCO$_3$ solution was added and 13 L H$_2$O was added and the mixture allowed to stir overnight at 20° C. The solid was then filtered off, washed with H$_2$O (4×4 L), and dried in vacuo to yield III (98.8%).

Example 20

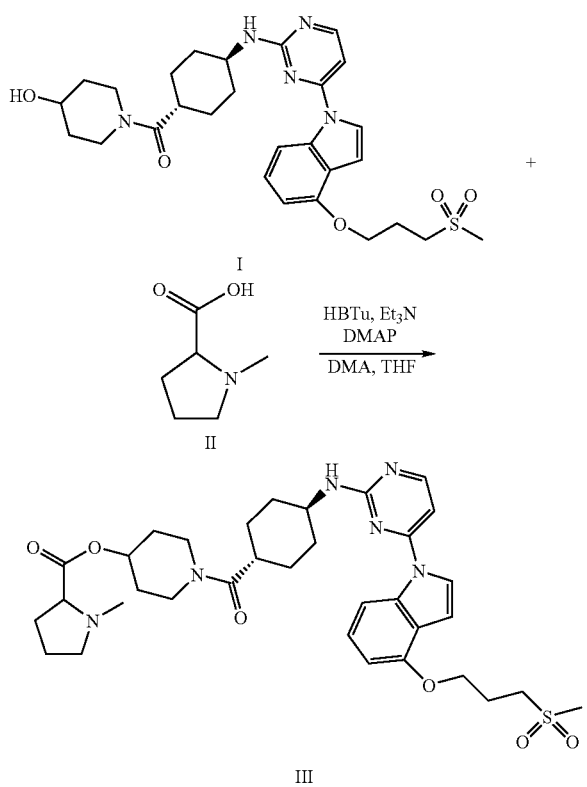

25 mL Et$_3$N and 33 g HBTU were added to 1 g II in 25 mL DMA. After 5 minutes of stirring at r.t., 25 g I was added, followed by the addition of 1.5 g DMAP, and the reaction allowed to stir for 6 h. The solvent was concentrated in vacuo, diluted with DCM, water added and the organic phase separated, washed with a sodium carbonate solution, H$_2$O, dried, and solvent removed in vacuo. The residue was suspended in EtOAc and allowed to crystallize over 2 days, the solid was then filtered, dissolved in hot THF (300 mL), filtered, and the solvent removed in vacuo. The residue was then recrystallized from 300 mL 2-butanone and 100 mL THF. The product was filtered off, washed with EtOAc, dried in vacuo at 50-60° C. overnight to give 18 g of III Biological Assays Example 21

JNK Assay In Vitro

JNK activity was measured by phosphorylation of GST-ATF2 (19-96) with [γ-$^{33}$P] ATP. The enzyme reaction was conducted at Km concentrations of ATP and the substrate at final volume of 40 µl in buffer containing 25 mM HEPES, pH 7.5, 2 mM dithiothreitol, 150 mM NaCl, 20 mM MgCl$_2$, 0.001% Tween® 20, 0.1% BSA and 10% DMSO. Human JNK2α2 assay contains 1 nM enzyme, 1 µM ATF2, 8 µM ATP with 1 uCi [γ-$^{33}$P] ATP. Human JNK1α1 assay contains 2 nM enzyme, 1 µM ATF2, 6 µM ATP with 1 µCi [γ-$^{33}$P] ATP. Human JNK3 Upstate Biotech #14-501M) assay contains 2 nM enzyme, 1 µM ATF2, 4 µM ATP with 1 µCi [γ-$^{33}$P] ATP. The enzyme assay was carried out in the presence or absence of several compound concentrations. JNK and compound were pre-incubated for 10 min., followed by initiation of the enzymatic reaction by adding ATP and the substrate. The reaction mixture was incubated at 30° C. for 30 min. At the end of incubation, the reaction was terminated by transferring 25 µl of the reaction mixture to 150 µl of 10% glutathione Sepharose® slurry (Amersham # 27-4574-01) containing 135 mM EDTA. The reaction product was captured on the affinity resin, and washed on a filtration plate (Millipore, MABVNOB50) with phosphate buffered saline for six times to remove free radionucleotide. The incorporation of $^{33}$P into ATF2 was quantified on a microplate scintillation counter (Packard Topcount). Compound inhibition potency on JNK was measured by IC$_{50}$ value generated from ten concentration inhibition curves fitted into the 3-parameter model: % inhibition=Maximum/(1+(IC$_{50}$/[Inhibitor])$^{slope}$). Data were analyzed on Microsoft Excel for parameter estimation. Representative results are shown in Table 1 below:

TABLE 1

Representative Compound IC$_{50}$'s for JNK1 and JNK2

| Compound | JNK1 (µM) | JNK2 (µM) |
| --- | --- | --- |
| I-1 | 0.0094 | 0.0408 |
| I-2 | 0.0068 | 0.0347 |
| I-3 | 0.0075 | 0.035 |
| I-4 | 0.0116 | 0.0519 |
| I-5 | 0.0074 | 0.0274 |
| I-6 | 0.0105 | 0.0402 |
| I-7 | 0.015 | 0.055 |
| I-8 | 0.0238 | 0.0676 |
| I-9 | 0.0153 | 0.0509 |
| I-11 | 0.0347 | 0.115 |
| I-12 | 0.0481 | 0.1617 |
| I-13 | 0.0108 | 0.0568 |
| I-14 | 0.0279 | 0.0679 |
| I-15 | 0.01 | 0.0405 |
| I-27 | 0.0176 | 0.0572 |

Example 22

Rat In Vivo TNFα-Induced IL-6 Production Assay

Female Wistar-Han rats procured from Charles River Laboratories were allowed to acclimate for one week prior to use and achieve an approximate body weight of 101-130 g.

Rats were administered test compound (N=8 per compound) via oral gavage 30 min prior to an intraperitoneal challenge of 0.5 µg recombinant rat TNF-α (Biosource). Blood was collected via cardiocentesis 90 min after TNF-α challenge. Plasma was prepared using lithium heparin separation tubes (BD microtainer) and frozen at −80° C. until analyzed. IL-6 levels were determined using a rat specific IL-6 ELISA kit (Biosource). The percent inhibition and $ED_{50}$ values (calculated as the dose of compound at which TNF-α production is 50% of the control value) were determined. The results are shown in Table 2 below:

TABLE 2

Inhibition of IL-6 Production

| Compound | Dose (mg/Kg) | IL-6 Inhibition (%) |
| --- | --- | --- |
| I-8 | 10 | 28.9 |
| I-8 | 30 | 40.2 |
| I-9 | 10 | 28.1 |
| I-9 | 30 | 49.1 |
| I-27 | 10 | 35.8 |
| I-27 | 30 | 50.7 |

Example 23

Rat In Vivo TNFα-Induced IL-6 Production Assay

Female Wistar-Han rats procured from Charles River Laboratories were allowed to acclimate for one week prior to use and achieve an approximate body weight of 114-132 g. Rats were administered compound 18 (N=8 per dose) subcutaneously 30 min prior to an intraperitoneal challenge of 0.5 µg recombinant rat TNF-α (Biosource). Blood was collected via cardiocentesis 90 min after TNF-α challenge. Plasma was prepared using lithium heparin separation tubes (BD microtainer) and frozen at −80° C. until analyzed. IL-6 levels were determined using a rat specific IL-6 ELISA kit (Biosource). The percent inhibition and $ED_{50}$ values (calculated as the dose of compound at which TNF-α production is 50% of the control value) were determined.

Example 24

Rodent Collagen-Induced Arthritis

Female Lewis rats procured from Harlan Laboratories at 7-8 weeks of age are allowed to acclimate for one week prior to use and achieve an approximate body weight of 120-140 g. On day 0 of study, rats are primed intradermally (i.d.) on several sites on the back with an emulsion of 100 µg Bovine Type II Collagen (Chondrex) in Incomplete Freund's adjuvant (IFA; total of 0.1 ml in 2-3 sites). Arthritis induction is generally observed 12-14 days from priming; however a booster injection of 100 µg collagen/IFA is given around days 7-10 (i.d. up to 0.1 ml total) at the base of the tail or an alternate site on back to synchronize disease induction. Compound dosing can be prophylactic (starting at time of boost or 1-2 days prior) or therapeutic (beginning after boost and coinciding with initial disease scores of 1-2—see clinical scoring below). Animals are evaluated for the development and progression of disease over the next 21 days.

Rats are evaluated using a scoring system (described below), paw volume measurements using a plethysmometer for each paw, or measuring paw or joint thickness with a caliper. Baseline measurements are performed on day 0, and starting again at the first signs of swelling for up to three times per week until the end of the experiment. Scoring is evaluated as follows for each paw:

1=swelling and/or redness of paw or one digit.
2=swelling in two or more joints.
3=gross swelling of the paw with more than two joints involved.
4=severe arthritis of the entire paw and digits.

The arthritic index for each rat is evaluated by adding the four scores of the individual paws, giving a maximum score of 16. In order to serially measure disease onset and progression, the paw volume of the hind paws is also determined through the use of a plethysmometer.

At the end of the study, the hind paws (and other tissues) are harvested for weight determination, histology, cellular and/or molecular analysis. Additionally, blood is collected via cardiocentesis, plasma is prepared using lithium heparin separation tubes (BD microtainer) and frozen at −70° C. until analyzed. Inflammatory cytokine levels (e.g., TNF-α, IL-1 and IL-6) from the plasma or from homogenized joint tissue are determined using rat-specific ELISA kits (R&D). The level of disease protection or inhibition is determined as a composite of changes in clinical scores, paw volumes and histopathology compared to control animals.

Example 25

Rat Pharmacokinetic Study

Female Wistar/Han (CRL: WI) Rats (Charles River, Hollister, Calif.) weighing between 180 and 220 g were used. Animals were allowed free access to a standard laboratory chow and tap water and were housed in a constant temperature-humidity environment. Three rats per dose regime were administered either single 10 mg/kg IV bolus doses (50% cyclodextran/water) or single 10 mg/kg oral suspension doses prepared in aqueous vehicle containing 0.9% NaCl, 0.5% sodium carboxymethyl cellulose, 0.4% polysorbate 80 and 0.9% benzyl alcohol. Blood was collected from each rat anesthetized with $CO_2:O_2$ (60:40) via the orbital sinus or cardiac puncture at 1, 3, 6, 8, and 24 h after dosing. Plasma levels of test compounds were assayed by a LC/MS method. In this method, an aliquot of plasma was treated by mixing with acetonitrile to precipitate protein, centrifuged to clarify the supernatant, then further diluted with formate buffer (50 mM), and injected onto an HPLC. Test compounds were separated from endogenous interfering substances and subsequently eluted from the HPLC column for mass spectrometric quantification.

The results are shown in Table 4 below:

TABLE 4

PK data in Rat.

| Compound | route/dose | Cmax* (ng/ml) | Tmax* (h) | AUC* (ng/ml-h) |
| --- | --- | --- | --- | --- |
| I-0 | po/100 mpk | 13500 | 0.67 | 36500 |
| I-4 | po/100 mpk | 7140 | 2.7 | 54500 |
| I-8 | po/100 mpk | 21500 | 0.6 | 47700 |
| I-9 | po/75 mpk | 13300 | 0.67 | 49400 |
| I-27 | po/98 mpk | 16900 | 0.67 | 53700 |

*the concentration of I-0 is measured for I-4, I-8, I-9, I-27.

While the present invention has been described with reference to the specific embodiments thereof, it should be understood by those skilled in the art that various changes may be made and equivalents may be substituted without departing

What is claimed is:
1. A compound of formula I

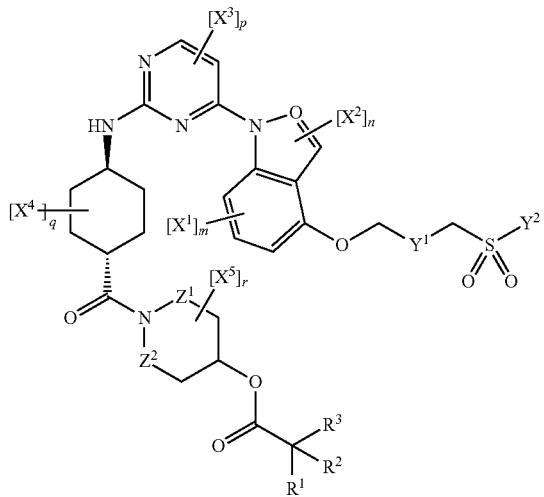

I or a pharmaceutically acceptable salt thereof,
wherein:
each of $R^1$ and $R^2$ is independently H or lower alkyl;
or $R^1$ and $R^2$ together form a cycloalkyl ring, optionally substituted with one or more $R^{2'}$;
$R^{2'}$ is lower alkyl, hydroxy, halogen, amino, lower alkoxy, lower hydroxyalkyl, or lower haloalkyl;
$R^3$ is H or $N(R^4)(R^5)$;
$R^4$ is H, lower alkyl, or $C(=O)OR^{4'}$;
$R^{4'}$ is H or lower alkyl;
$R^5$ is H or lower alkyl;
or $R^2$ and $R^3$ together form a heterocyclic or heteroaryl ring, optionally substituted with one or more $R^{2'}$;
Q is CH or N;
$Z^1$ is $(CH_2)_u$;
u is 0 or 1;
$Z^2$ is $(CH_2)_v$;
v is 0 or 1;
$X^1$ is lower alkyl, lower alkoxy, lower haloalkyl, or hydroxy;
m is 0, 1, or 2;
$X^2$ is lower alkyl, lower alkoxy, or lower haloalkyl;
n is 0 or 1;
$X^3$ is lower alkyl, lower alkoxy, or lower haloalkyl;
p is 0 or 1;
$X^4$ is lower alkyl, lower alkoxy, lower haloalkyl, hydroxy, lower hydroxylalkyl, or halogen;
q is 0, 1, or 2;
$X^5$ is lower alkyl, lower alkoxy, lower haloalkyl, hydroxy, lower hydroxylalkyl, or halogen;
r is 0, 1, or 2;
$Y^1$ is $CH(Y^{1'})$;
$Y^{1'}$ is H or lower alkyl;
$Y^2$ is H or $Y^{2'}$;
$Y^{2'}$ is lower alkyl, $N(Y^{2''})_2$, lower haloalkyl, or lower heteroalkyl;
or $Y^{1'}$ and $Y^{2'}$ together form a heterocyclic ring; and
each $Y^{2''}$ is independently H, lower alkyl, lower cycloalkyl, phenyl, or lower heterocycloalkyl;
or both $Y^{2''}$ together form a heterocyclic ring.

2. The compound of claim 1, wherein m is 0, n is 0, p is 0, Q is CH, q is 0, $R^1$ is H, r is 0, u is 1, v is 1, $Y^{1'}$ is H, $Y^2$ is $Y^{2'}$, and $Y^{2'}$ is methyl.

3. The compound of claim 1, wherein m is 0, n is 0, p is 0, Q is CH, q is 0, $R^1$ is H, r is 0, u is 1, v is 1, $Y^2$ is $Y^{2'}$, and $Y^{1'}$ and $Y^{2'}$ together form a heterocyclic ring.

4. The compound of claim 1, wherein m is 0, n is 0, p is 0, Q is CH, q is 0, $R^1$ is H, r is 0, u is 1, v is 1, $Y^{1''}$ is H, $Y2$ is $Y^{2'}$, Y2' is $N(Y^{2''})_2$, and both $Y^{2''}$ are H.

5. A compound of formula II

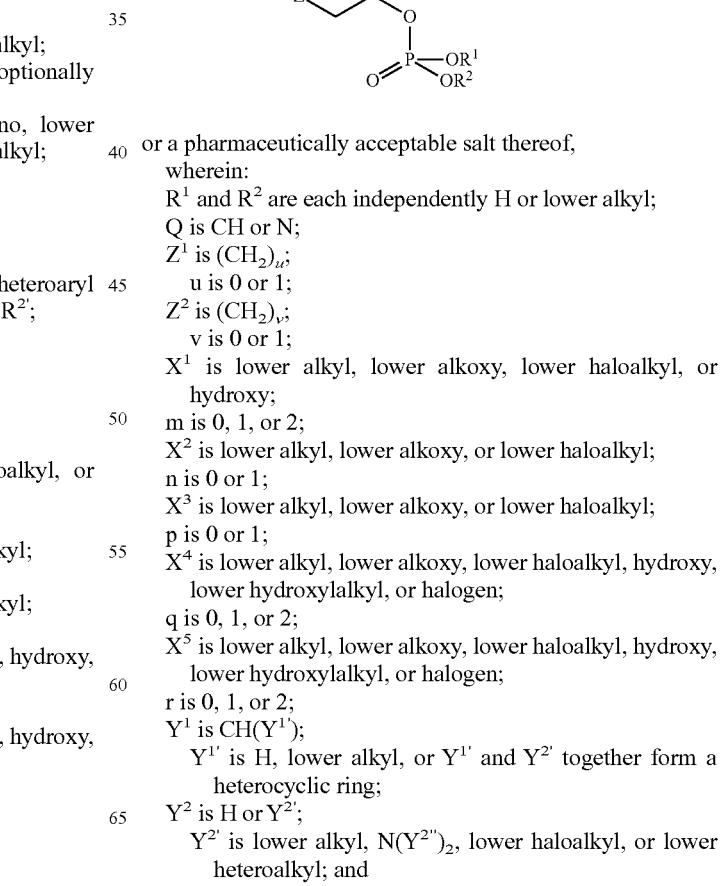

II or a pharmaceutically acceptable salt thereof,
wherein:
$R^1$ and $R^2$ are each independently H or lower alkyl;
Q is CH or N;
$Z^1$ is $(CH_2)_u$;
u is 0 or 1;
$Z^2$ is $(CH_2)_v$;
v is 0 or 1;
$X^1$ is lower alkyl, lower alkoxy, lower haloalkyl, or hydroxy;
m is 0, 1, or 2;
$X^2$ is lower alkyl, lower alkoxy, or lower haloalkyl;
n is 0 or 1;
$X^3$ is lower alkyl, lower alkoxy, or lower haloalkyl;
p is 0 or 1;
$X^4$ is lower alkyl, lower alkoxy, lower haloalkyl, hydroxy, lower hydroxylalkyl, or halogen;
q is 0, 1, or 2;
$X^5$ is lower alkyl, lower alkoxy, lower haloalkyl, hydroxy, lower hydroxylalkyl, or halogen;
r is 0, 1, or 2;
$Y^1$ is $CH(Y^{1'})$;
$Y^{1'}$ is H, lower alkyl, or $Y^{1'}$ and $Y^{2'}$ together form a heterocyclic ring;
$Y^2$ is H or $Y^{2'}$;
$Y^{2'}$ is lower alkyl, $N(Y^{2''})_2$, lower haloalkyl, or lower heteroalkyl; and each Y²" is independently H, lower alkyl, lower cycloalkyl, phenyl, lower heterocycloalkyl, or both Y²" together form a heterocyclic ring.

6. The compound of claim 5, wherein m is 0, n is 0, p is 0, Q is CH, q is 0, R¹ is H, r is 0, u is 1, v is 1, Y¹' is H, Y² is Y²', and Y²' is methyl.

7. A compound of formula III

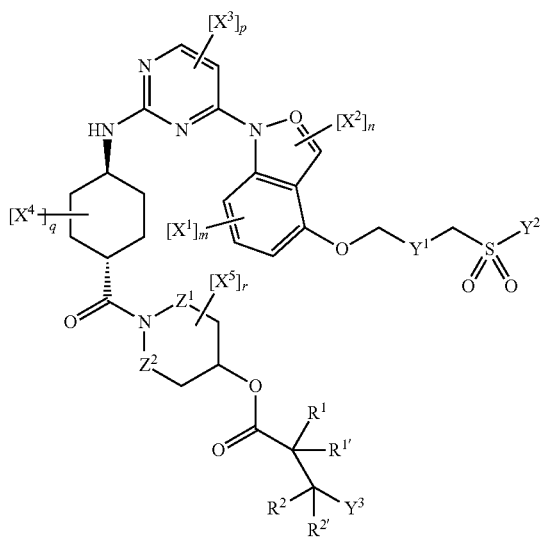

or a pharmaceutically acceptable salt thereof,
wherein:
R¹ and R¹' are each independently H or lower alkyl;
R² is H or lower alkyl;
R²' and R³ are each independently H or lower alkyl, or R²' and R³ together form a heterocyclic ring, optionally substituted with one or more R³';
R³' is lower alkyl, hydroxy, halogen, lower heteroalkyl, lower alkoxy, lower hydroxyalkyl, or lower haloalkyl;
R⁴ and R⁵ are each independently H or lower alkyl;
Q is CH or N;
Z¹ is (CH₂)ᵤ;
u is 0 or 1;
Z² is (CH₂)ᵥ;
v is 0 or 1;
X¹ is lower alkyl, lower alkoxy, lower haloalkyl, or hydroxy;
m is 0, 1, or 2;
X² is lower alkyl, lower alkoxy, or lower haloalkyl;
n is 0 or 1;
X³ is lower alkyl, lower alkoxy, or lower haloalkyl;
p is 0 or 1;
X⁴ is lower alkyl, lower alkoxy, lower haloalkyl, hydroxy, lower hydroxylalkyl, or halogen;
q is 0, 1, or 2;
X⁵ is lower alkyl, lower alkoxy, lower haloalkyl, hydroxy, lower hydroxylalkyl, or halogen;
r is 0, 1, or 2;
Y¹ is CH(Y¹');
Y¹' is H or lower alkyl;
Y² is H or Y²';
Y²' is lower alkyl, N(Y²")₂, lower haloalkyl, or lower heteroalkyl;
or Y¹' and Y²' together form a heterocyclic ring;

each Y²" is independently H, lower alkyl, lower cycloalkyl, phenyl, or lower heterocycloalkyl;
or both Y²" together form a heterocyclic ring; and
Y³ is N(R³)(R⁴) or N(R³)(R⁴)(R⁵)⁺.

8. The compound of claim 7, wherein m is 0, n is 0, p is 0, Q is CH, q is 0, R¹ is H, r is 0, u is 1, v is 1, Y¹' is H, Y² is Y²', and Y²' is methyl.

9. A compound of formula IV

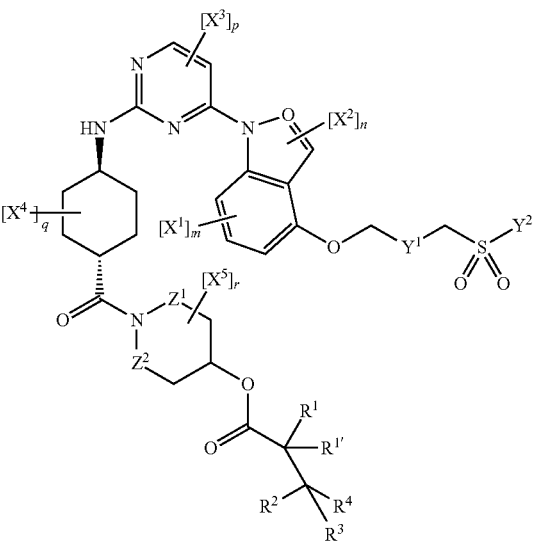

or a pharmaceutically acceptable salt thereof,
wherein:
R¹ and R¹" are each independently H or lower alkyl;
R² and R³ are each independently H or lower alkyl;
R⁴ is H, lower alkyl, lower alkoxy, or —C(=O)OR¹;
Q is CH or N;
Z¹ is (CH₂)ᵤ;
u is 0 or 1;
Z² is (CH₂)ᵥ;
v is 0 or 1;
X¹ is lower alkyl, lower alkoxy, lower haloalkyl, or hydroxy;
m is 0, 1, or 2;
X² is lower alkyl, lower alkoxy, or lower haloalkyl;
n is 0 or 1;
X³ is lower alkyl, lower alkoxy, or lower haloalkyl;
p is 0 or 1;
X⁴ is lower alkyl, lower alkoxy, lower haloalkyl, hydroxy, lower hydroxylalkyl, or halogen;
q is 0, 1, or 2;
X⁵ is lower alkyl, lower alkoxy, lower haloalkyl, hydroxy, lower hydroxylalkyl, or halogen;
r is 0, 1, or 2;
Y¹ is CH(Y¹');
Y¹' is H or lower alkyl;
Y² is H or Y²';
Y²' is lower alkyl, N(Y²")₂, lower haloalkyl, or lower heteroalkyl;
or Y¹' and Y²' together form a heterocyclic ring; and
each Y²" is independently H, lower alkyl, lower cycloalkyl, phenyl, or lower heterocycloalkyl;
or both Y²" together form a heterocyclic ring.

10. The compound of claim 9, m is 0, n is 0, p is 0, Q is CH, q is 0, $R^1$ is H, r is 0, u is 1, v is 1, $Y^{1'}$ is H, $Y^2$ is $Y^{2'}$, and $Y^{2'}$ is methyl.

11. A compound of formula V

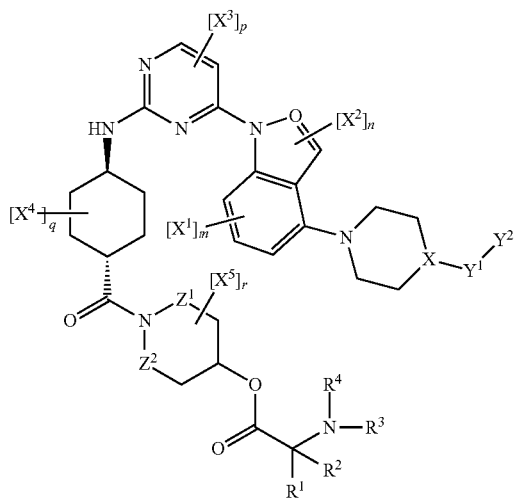

or a pharmaceutically acceptable salt thereof,
wherein:
$R^1$ is H or lower alkyl, or $R^1$ and $R^2$ together form a cycloalkyl ring, optionally substituted with one or more $R^{2'}$;
$R^{2'}$ is lower alkyl, hydroxy, halogen, lower heteroalkyl, lower alkoxy, lower hydroxyalkyl, or lower haloalkyl;
$R^2$ and $R^3$ are each independently H or lower alkyl, or $R^2$ and $R^3$ together form a heterocyclic ring, optionally substituted with one or more $R^{2'}$;
$R^4$ is H or lower alkyl;
Q is CH or N;
$Z^1$ is $(CH_2)_u$;
u is 0 or 1;
$Z^2$ is $(CH_2)_v$;
v is 0 or 1;
X is N or CH;
$X^1$ is lower alkyl, lower alkoxy, lower haloalkyl, or hydroxy;
m is 0, 1, or 2;
$X^2$ is lower alkyl, lower alkoxy, or lower haloalkyl;
n is 0 or 1;
$X^3$ is lower alkyl, lower alkoxy, or lower haloalkyl;
p is 0 or 1;
$X^4$ is lower alkyl, lower alkoxy, lower haloalkyl, hydroxy, lower hydroxyalkyl, or halogen;
q is 0, 1, or 2;
$X^5$ is lower alkyl, lower alkoxy, lower haloalkyl, hydroxy, lower hydroxyalkyl, or halogen;
r is 0, 1, or 2;
$Y^1$ is C(=O) or S(=O)$_2$;
$Y^2$ is H or $Y^{2'}$;
$Y^{2'}$ is lower alkyl, $N(Y^{2''})_2$, lower haloalkyl, or lower heteroalkyl; and
each $Y^{2''}$ is independently H, lower alkyl, lower cycloalkyl, phenyl, lower heterocycloalkyl, or both $Y^{2''}$ together form a heterocyclic ring.

12. The compound of claim 11, m is 0, n is 0, p is 0, Q is CH, q is 0, $R^1$ is H, r is 0, u is 1, and v is 1.

13. A compound selected from the group consisting of:
(S)-2-Amino-propionic acid 1-(4-{4-[4-(3-methanesulfonyl-propoxy)-indol-1-yl]-pyrimidin-2-ylamino}-cyclohexanecarbonyl)-piperidin-4-yl ester;
2-Amino-2-methyl-propionic acid 1-(4-{4-[4-(3-methanesulfonyl-propoxy)-indol-1-yl]-pyrimidin-2-ylamino}-cyclohexanecarbonyl)-piperidin-4-yl ester;
(S)-2-Amino-4-methyl-pentanoic acid 1-(4-{4-[4-(3-methanesulfonyl-propoxy)-indol-1-yl]-pyrimidin-2-ylamino}-cyclohexanecarbonyl)-piperidin-4-yl ester;
(2S,3S)-2-Amino-3-methyl-pentanoic acid 1-(4-{4-[4-(3-methanesulfonyl-propoxy)-indol-1-yl]-pyrimidin-2-ylamino}-cyclohexanecarbonyl)-piperidin-4-yl ester;
(S)-Pyrrolidine-2-carboxylic acid 1-(4-{4-[4-(3-methanesulfonyl-propoxy)-indol-1-yl]-pyrimidin-2-ylamino}-cyclohexanecarbonyl)-piperidin-4-yl ester;
(S)-2-Amino-3-methyl-butyric acid 1-(4-{4-[4-(3-methanesulfonyl-propoxy)-indol-1-yl]-pyrimidin-2-ylamino}-cyclohexanecarbonyl)-piperidin-4-yl ester;
(R)-1-Methyl-pyrrolidine-2-carboxylic acid 1-(4-{4-[4-(3-methanesulfonyl-propoxy)-indol-1-yl]-pyrimidin-2-ylamino}-cyclohexanecarbonyl)-piperidin-4-yl ester;
Dimethylamino-acetic acid 1-(4-{4-[4-(3-methanesulfonyl -propoxy)-indol-1-yl]-pyrimidin-2-ylamino}-cyclohexanecarbonyl)-piperidin-4-yl ester;
(S)-2-Methylamino-propionic acid 1-(4-{4-[4-(3-methanesulfonyl-propoxy)-indol-1-yl]-pyrimidin-2-ylamino}-cyclohexanecarbonyl)-piperidin-4-yl ester;
(2R,3S)-2-Amino-3-methyl-pentanoic acid 1-(4-{4-[4-(3-methanesulfonyl-propoxy)-indol-1-yl]-pyrimidin-2-ylamino}-cyclohexanecarbonyl)-piperidin-4-yl ester;
(2R,3R)-2-Amino-3-methyl-pentanoic acid 1-(4-{4-[4-(3-methanesulfonyl-propoxy)-indol-1-yl]-pyrimidin-2-ylamino}-cyclohexanecarbonyl)-piperidin-4-yl ester;
Phosphoric acid 1-(4-{4-[4-(3-methanesulfonyl-propoxy)-indol-1-yl]-pyrimidin-2-ylamino}-cyclohexanecarbonyl)-piperidin-4-yl ester dimethyl ester;
Phosphoric acid mono-[1-(4-{4-[4-(3-methanesulfonyl -propoxy)-indol-1-yl]-pyrimidin-2-ylamino}-cyclohexanecarbonyl)-piperidin-4-yl]ester;
Succinic acid mono-[1-(4-{4-[4-(3-methanesulfonyl -propoxy)-indol-1-yl]-pyrimidin-2-ylamino}-cyclohexanecarbonyl)-piperidin-4-yl]ester;
(R)-3-Methyl-2-methylamino-butyric acid 1-(4-{4-[4-(3-methanesulfonyl-propoxy)-indol-1-yl]-pyrimidin-2-ylamino}-cyclohexanecarbonyl)-piperidin-4-yl ester;
(2R,3R)-3-Methyl-2-methylamino-pentanoic acid 1-(4-{4-[4-(3-methanesulfonyl-propoxy) -indol-1-yl]-pyrimidin-2-ylamino}-cyclohexanecarbonyl)-piperidin-4-yl ester;
(S)-1-Ethyl-pyrrolidine-2-carboxylic acid 1-(4-{4-[4-(3-methanesulfonyl-propoxy)-indol-1-yl]-pyrimidin-2-ylamino}-cyclohexanecarbonyl)-piperidin-4-yl ester;
1-Methylamino-cyclopropanecarboxylic acid 1-(4-{4-[4-(3-methanesulfonyl-propoxy)-indol-1-yl]-pyrimidin-2-ylamino}-cyclohexanecarbonyl)-piperidin-4-yl ester;
(S)-1-Methyl-piperidine-2-carboxylic acid 1-(4-{4-[4-(3-methanesulfonyl-propoxy)-indol-1-yl]-pyrimidin-2-ylamino}-cyclohexanecarbonyl)-piperidin-4-yl ester;
3-Amino-propionic acid 1-(4-{4-[4-(3-methanesulfonyl-propoxy)-indol-1-yl]-pyrimidin-2-ylamino}-cyclohexanecarbonyl)-piperidin-4-yl ester;
3-Dimethylamino-propionic acid 1-(4-{4-[4-(3-methanesulfonyl-propoxy)-indol-1-yl]-pyrimidin-2-ylamino}-cyclohexanecarbonyl)-piperidin-4-yl ester;

Trimethylammonium-propionic acid 1-(4-{4-[4-(3-methanesulfonyl-propoxy)-indol-1-yl]-pyrimidin-2-ylamino}-cyclohexanecarbonyl)-piperidin-4-yl ester;

Amino-acetic acid 1-(4-{4-[4-(3-methanesulfonyl-propoxy)-indol-1-yl]-pyrimidin-2-ylamino}-cyclohexanecarbonyl)-piperidin-4-yl ester;

Methylamino-acetic acid 1-(4-{4-[4-(3-methanesulfonyl-propoxy)-indol-1-yl]-pyrimidin-2-ylamino}-cyclohexanecarbonyl)-piperidin-4-yl ester;

Propionic acid 1-(4-{[4-(3-methanesulfonyl-propoxy)-indol-1-yl]-pyrimidin-2-ylamino}-cyclohexanecarbonyl)-piperidin-4-yl ester;

(S)-4-Hydroxy-1-methyl-pyrrolidine-2-carboxylic acid 1-(4-{4-[4-(3-methanesulfonyl -propoxy)-indol-1-yl]-pyrimidin-2-ylamino}-cyclohexanecarbonyl)-piperidin-4-yl ester;

(S)-1-Methyl-pyrrolidine-2-carboxylic acid 1-(4-{4-[4-(3-methanesulfonyl-propoxy)-indol-1-yl]-pyrimidin-2-ylamino}-cyclohexanecarbonyl)-piperidin-4-yl ester;

Acetic acid 1-(4-{4-[4-(3-methanesulfonyl-propoxy)-indol -1-yl]-pyrimidin-2-ylamino}-cyclohexanecarbonyl)-piperidin-4-yl ester;

Nicotinic acid 1-(4-{4-[4-(3-methanesulfonyl-propoxy)-indol-1-yl]-pyrimidin-2-ylamino}-cyclohexanecarbonyl)-piperidin-4-yl ester;

(2R,3R)-2-(tert-Butoxycarbonyl-methyl-amino)-3-methyl-pentanoic acid 1(4-{4-[4-(3-methanesulfonyl-propoxy)-indol-1-yl]-pyrimidin-2-ylamino}-cyclohexanecarbonyl) -piperidin-4-yl ester; and (R)-2-(tert-Butoxycarbonyl-methyl-amino)-3-methyl-butyric acid 1-(4-{4-[4-(3-methanesulfonyl-propoxy)-indol-1-yl]-pyrimidin-2-ylamino}-cyclohexanecarbonyl) -piperidin-4-yl ester.

14. A process for making the compound of claim 1, comprising the steps of:
    a) reacting 4-(3-methylsulfanyl-propoxy)-1H-indole with 4-chloro-2-methylsulfanyl-pyrimidine;
    b) reacting the product of step a) with an oxidizing agent;
    c) reacting the product of step b) with 4-amino-cyclohexanecarboxylic acid ethyl ester or pharmaceutically acceptable salt thereof;
    d) reacting the product of step c) with a base;
    e) reacting the product of step d) with piperidin-4-ol and 2-(1H -benzotriazol-1-yl)-1,1,3,3,-tetramethyluronium hexafluorophosphate; and
    f) reacting the product of step e) with a substituted or unsubstituted amino acid and 2-(1H-benzotriazol-1-yl)-1,1,3,3,-tetramethyluronium hexafluorophosphate.

15. A process for making the compound of claim 1, comprising the steps of:
    a) reacting 4-(3-methanesulfonyl-propoxy)-1H-indole with 2,4-dichloro-pyrimidine in the presence of 1-Hydroxybenzotriazole;
    b) reacting the product of step a) with 4-amino-cyclohexanecarboxylic acid ethyl ester or pharmaceutically acceptable salt thereof;
    c) reacting the product of step b) with a base;
    d) reacting the product of step c) with piperidin-4-ol and 2-(1H -benzotriazol-1-yl)-1,1,3,3,-tetramethyluronium hexafluorophosphate; and
    e) reacting the product of step d) with a substituted or unsubstituted amino acid and 2-(1H-benzotriazol-1-yl)-1,1,3,3,-tetramethyluronium hexafluorophosphate.

16. A method of treating a JNK-mediated disorder in a subject having a JNK-mediated disorder, said method comprising administering to a subject in need thereof a therapeutically effective amount of the compound of claim 1, wherein the JNK-mediated disorder is diabetes, arthritis, asthma, Alzheimer's disease, Parkinson's disease or ischemic stroke.

17. The method of claim 16, wherein the JNK-mediated disorder is arthritis.

18. The method of claim 17, wherein the arthritis is rheumatoid arthritis.

19. The method of claim 16, wherein the JNK-mediated disorder is asthma.

20. The method of claim 16, wherein the JNK-mediated disorder is Alzheimer's disease or Parkinson's disease.

21. The method of claim 16, wherein the JNK-mediated disorder is ischemic stroke.

22. A pharmaceutical composition comprising the compound of claim 1, admixed with at least one pharmaceutically acceptable carrier, excipient or diluent.

* * * * *

UNITED STATES PATENT AND TRADEMARK OFFICE
CERTIFICATE OF CORRECTION

PATENT NO.       : 8,183,254 B2
APPLICATION NO.  : 12/454210
DATED            : May 22, 2012
INVENTOR(S)      : Arzeno et al.

Page 1 of 1

It is certified that error appears in the above-identified patent and that said Letters Patent is hereby corrected as shown below:

Claim 4, column 78, line 14, end of line, delete "$_y2$ is $Y^{2'}$," and insert -- $Y^2$ is $Y^{2'}$, --

Signed and Sealed this
Tenth Day of July, 2012

David J. Kappos
*Director of the United States Patent and Trademark Office*